US011663896B2

(12) United States Patent
Kazerouni

(10) Patent No.: US 11,663,896 B2
(45) Date of Patent: May 30, 2023

(54) COMPREHENSIVE SYSTEM AND METHOD OF UNIVERSAL REAL-TIME LINKING OF REAL OBJECTS TO A MACHINE, NETWORK, INTERNET, OR SOFTWARE SERVICE

(71) Applicant: LINQUET TECHNOLOGIES, INC., Vancouver (CA)

(72) Inventor: Pooya H. Kazerouni, Vancouver (CA)

(73) Assignee: LINQUET TECHNOLOGIES, INC., Vancouver (CA)

( * ) Notice: Subject to any disclaimer, the term of this patent is extended or adjusted under 35 U.S.C. 154(b) by 0 days.

(21) Appl. No.: 17/704,348

(22) Filed: Mar. 25, 2022

(65) Prior Publication Data

US 2022/0215735 A1 Jul. 7, 2022

Related U.S. Application Data

(63) Continuation of application No. 17/014,895, filed on Sep. 8, 2020, which is a continuation of application
(Continued)

(51) Int. Cl.
*G08B 21/02* (2006.01)
*G06K 19/07* (2006.01)
(Continued)

(52) U.S. Cl.
CPC .......... *G08B 21/0269* (2013.01); *G01S 3/782* (2013.01); *G01S 5/02* (2013.01);
(Continued)

(58) Field of Classification Search
CPC ............ G08B 21/0269; G08B 13/1427; G08B 13/2462; G08B 21/0247; G08B 21/0275;
(Continued)

(56) References Cited

U.S. PATENT DOCUMENTS 4,384,288 A 5/1983 Walton
4,682,155 A 7/1987 Shirley
(Continued)

FOREIGN PATENT DOCUMENTS

CN 101883259 A 11/2010
CN 101930066 A 12/2010
(Continued)

OTHER PUBLICATIONS

Amended Complaint for Patent Infringement, dated Oct. 29, 2020, United States District Court Northern District of California, Case 3:20-cv-05153-NC, p. 14.
(Continued)

*Primary Examiner* — Kerri L McNally
(74) *Attorney, Agent, or Firm* — Faegre Drinker Biddle & Reath LLP

(57) ABSTRACT

A system for detecting placement or misplacement of an object includes a wireless tag; a first electronic device ("FED") associated with the tag to automatically detect signals from the tag, determine a position of the FED, transmit the position and status to an external electronic device or network ("EED") in response to the status indicating that the tag and the FED are within a predetermined range, and transmit the position and status to the EED in response to the status indicating that the tag and the FED are outside of the predetermined range; and a second electronic device ("SED") that is unassociated with the tag to automatically detect signals from the tag, determine a position of the SED, determine an identifier for the tag using the signals, and transmit the position of the SED and the identifier to the EED.

5 Claims, 21 Drawing Sheets

Related U.S. Application Data

No. 16/227,572, filed on Dec. 20, 2018, now Pat. No. 10,769,924, which is a continuation-in-part of application No. 16/005,193, filed on Jun. 11, 2018, now Pat. No. 10,163,318, which is a continuation of application No. 15/156,726, filed on May 17, 2016, now Pat. No. 9,997,043, which is a continuation of application No. 14/617,240, filed on Feb. 9, 2015, now Pat. No. 9,366,746, which is a continuation of application No. 13/754,607, filed on Jan. 30, 2013, now Pat. No. 8,981,938.

(60) Provisional application No. 61/608,429, filed on Mar. 8, 2012.

(51) Int. Cl.
| | | |
|---|---|---|
| *G08B 13/14* | (2006.01) | |
| *G06K 7/10* | (2006.01) | |
| *G06K 19/077* | (2006.01) | |
| *G01S 3/782* | (2006.01) | |
| *G08B 13/24* | (2006.01) | |
| *G16H 40/20* | (2018.01) | |
| *G16H 10/65* | (2018.01) | |
| *G01S 5/02* | (2010.01) | |
| *G06K 19/06* | (2006.01) | |

(52) U.S. Cl.
CPC ..... *G06K 7/10297* (2013.01); *G06K 19/0716* (2013.01); *G06K 19/0717* (2013.01); *G06K 19/0772* (2013.01); *G06K 19/07713* (2013.01); *G06K 19/07749* (2013.01); *G08B 13/1427* (2013.01); *G08B 13/2462* (2013.01); *G08B 21/0247* (2013.01); *G08B 21/0275* (2013.01); *G08B 21/0277* (2013.01); *G16H 10/65* (2018.01); *G16H 40/20* (2018.01); *G06K 2019/06253* (2013.01); *G06K 2019/06281* (2013.01); *G08B 21/0272* (2013.01)

(58) Field of Classification Search
CPC .... G08B 21/0277; G16H 40/20; G16H 10/65; G01S 3/782; G01S 5/02; G06K 7/10297; G06K 19/0716; G06K 19/0717; G06K 19/07713; G06K 19/0772; G06K 19/07749
USPC ...................................................... 340/572.1
See application file for complete search history.

(56) References Cited

U.S. PATENT DOCUMENTS

| | | |
|---|---|---|
| 5,297,737 A | 3/1994 | Davisson |
| 5,731,757 A | 3/1998 | Layson, Jr. |
| 5,973,599 A | 10/1999 | Nicholson et al. |
| 6,058,309 A | 5/2000 | Huang et al. |
| 6,297,737 B1 | 10/2001 | Irvin |
| 6,321,095 B1 | 11/2001 | Gavette |
| 6,594,666 B1 | 7/2003 | Biswas et al. |
| 6,717,516 B2 | 4/2004 | Bridgelall |
| 6,967,576 B2 | 11/2005 | Hayes et al. |
| 6,998,985 B2 | 2/2006 | Reisman et al. |
| 7,034,684 B2 | 4/2006 | Boman et al. |
| 7,114,175 B2 | 9/2006 | Laehteenmaeki |
| 7,248,167 B2 | 7/2007 | Wassingbo |
| D555,019 S | 11/2007 | Au Yeung |
| 7,323,991 B1 | 1/2008 | Eckert et al. |
| 7,420,465 B2 | 9/2008 | Ritter |
| 7,502,619 B1 | 3/2009 | Katz |
| 7,516,890 B1 | 4/2009 | Spremo et al. |
| 7,589,616 B2 | 9/2009 | Klatsmanyi et al. |
| D611,366 S | 3/2010 | Register et al. |
| D615,427 S | 5/2010 | Au Yeung |
| D617,667 S | 6/2010 | Penix et al. |
| D618,121 S | 6/2010 | Penix et al. |
| 7,843,343 B2 | 11/2010 | Thorn |
| D632,984 S | 2/2011 | Register et al. |
| D635,874 S | 4/2011 | Tseng et al. |
| D637,097 S | 5/2011 | Tseng |
| D644,542 S | 9/2011 | Henne et al. |
| 8,014,789 B2 | 9/2011 | Breed |
| 8,045,954 B2 | 10/2011 | Barbeau et al. |
| RE42,996 E | 12/2011 | Hyun et al. |
| 8,094,012 B1 | 1/2012 | Tran et al. |
| 8,094,912 B2 | 1/2012 | Miyamoto et al. |
| D659,569 S | 5/2012 | Shadovitz |
| D665,679 S | 8/2012 | Shigeno et al. |
| D665,680 S | 8/2012 | Shigeno et al. |
| 8,280,351 B1 | 10/2012 | Ahmed et al. |
| D674,715 S | 1/2013 | Dalton |
| D677,589 S | 3/2013 | Jung et al. |
| D682,126 S | 5/2013 | Tello |
| D684,071 S | 6/2013 | Greenwood et al. |
| 8,506,524 B2 | 8/2013 | Graaskov et al. |
| 8,551,186 B1 | 10/2013 | Strand |
| D693,248 S | 11/2013 | Anderssen et al. |
| D693,249 S | 11/2013 | Anderssen et al. |
| D693,250 S | 11/2013 | Anderssen et al. |
| 8,611,321 B2 | 12/2013 | Herrala et al. |
| D699,131 S | 2/2014 | Marshall et al. |
| D700,084 S | 2/2014 | Hsu |
| D702,141 S | 4/2014 | Jung et al. |
| 8,704,657 B2 * | 4/2014 | Huang ............... G08B 13/1427 340/539.21 |
| 8,810,392 B1 * | 8/2014 | Teller .................... G08B 21/24 340/572.1 |
| 8,817,712 B2 | 8/2014 | Shin et al. |
| 8,839,386 B2 | 9/2014 | Gilboy |
| 8,869,248 B2 | 10/2014 | Moosavi et al. |
| 8,938,775 B1 | 1/2015 | Roth et al. |
| D723,957 S | 3/2015 | Evans et al. |
| 8,981,938 B2 | 3/2015 | Pooya |
| D728,393 S | 5/2015 | Au Yeung |
| D729,655 S | 5/2015 | Bauer et al. |
| D731,334 S | 6/2015 | Fiedler et al. |
| 9,069,994 B1 | 6/2015 | Strand |
| 9,245,433 B1 | 1/2016 | Butler et al. |
| D748,507 S | 2/2016 | Evans et al. |
| D750,478 S | 3/2016 | Kiss |
| 9,357,348 B2 | 5/2016 | Evans et al. |
| 9,366,746 B2 | 6/2016 | Kazerouni |
| 9,525,970 B2 | 12/2016 | Farley et al. |
| 9,615,210 B2 | 4/2017 | Evans et al. |
| 9,699,612 B2 | 7/2017 | Evans et al. |
| 9,997,043 B2 | 6/2018 | Pooya |
| 10,163,318 B2 | 12/2018 | Pooya |
| 10,769,924 B2 | 9/2020 | Pooya |
| 2002/0061748 A1 | 5/2002 | Nakakita et al. |
| 2002/0147650 A1 | 10/2002 | Kaufman et al. |
| 2003/0095032 A1 | 5/2003 | Hoshino et al. |
| 2003/0181215 A1 | 9/2003 | Cromer et al. |
| 2003/0207683 A1 | 11/2003 | Lempio et al. |
| 2003/0233458 A1 | 12/2003 | Kwon et al. |
| 2003/0235172 A1 | 12/2003 | Wood |
| 2004/0174264 A1 | 9/2004 | Reisman et al. |
| 2004/0192352 A1 | 9/2004 | Vallstrom et al. |
| 2004/0198389 A1 | 10/2004 | Alcock et al. |
| 2005/0200478 A1 | 9/2005 | Koch et al. |
| 2006/0046689 A1 | 3/2006 | Kim |
| 2006/0158310 A1 | 7/2006 | Klatsmanyi et al. |
| 2006/0182055 A1 | 8/2006 | Coffee et al. |
| 2006/0229896 A1 | 10/2006 | Rosen et al. |
| 2007/0009237 A1 | 1/2007 | Kunita |
| 2007/0113092 A1 | 5/2007 | Nishida et al. |
| 2007/0167175 A1 | 7/2007 | Wong et al. |
| 2007/0176771 A1 * | 8/2007 | Doyle ................ G08B 13/1427 340/539.13 |
| 2007/0194926 A1 | 8/2007 | Bayley et al. |
| 2007/0229350 A1 | 10/2007 | Scalisi et al. |
| 2007/0257803 A1 | 11/2007 | Munro et al. |
| 2008/0062120 A1 | 3/2008 | Wheeler et al. |

(56) References Cited

U.S. PATENT DOCUMENTS

| | | |
|---|---|---|
| 2008/0086391 A1 | 4/2008 | Maynard et al. |
| 2008/0129485 A1 | 6/2008 | Tuttle |
| 2008/0143516 A1 | 6/2008 | Mock et al. |
| 2008/0172173 A1 | 7/2008 | Chang et al. |
| 2008/0182592 A1 | 7/2008 | Cha et al. |
| 2008/0186162 A1 | 8/2008 | Rajan et al. |
| 2008/0191846 A1 | 8/2008 | Chang |
| 2008/0211671 A1 | 9/2008 | Daily |
| 2008/0287143 A1 | 11/2008 | Banks et al. |
| 2008/0303901 A1 | 12/2008 | Variyath et al. |
| 2009/0002188 A1 | 1/2009 | Greenberg |
| 2009/0079544 A1 | 3/2009 | Noble |
| 2009/0224892 A1 | 9/2009 | Nicholls |
| 2009/0239502 A1 | 9/2009 | Dempo et al. |
| 2009/0322510 A1 | 12/2009 | Berger et al. |
| 2010/0080175 A1 | 4/2010 | Kang et al. |
| 2010/0141430 A1 | 6/2010 | Steer |
| 2010/0164714 A1 | 7/2010 | Buller et al. |
| 2010/0164715 A1 | 7/2010 | Buller et al. |
| 2010/0194531 A1 | 8/2010 | Sato |
| 2010/0199339 A1 | 8/2010 | Kageyama |
| 2010/0273452 A1 | 10/2010 | Rajann et al. |
| 2010/0283600 A1 | 11/2010 | Herbert et al. |
| 2010/0289646 A1* | 11/2010 | Raniere ............... G08B 21/24 340/568.1 |
| 2011/0051665 A1 | 3/2011 | Huang |
| 2011/0068923 A1 | 3/2011 | Burket et al. |
| 2011/0087685 A1 | 4/2011 | Lin et al. |
| 2011/0140884 A1* | 6/2011 | Santiago ............. G01S 5/0027 340/539.13 |
| 2011/0195701 A1 | 8/2011 | Cook et al. |
| 2011/0231092 A1 | 9/2011 | Kuo et al. |
| 2011/0234399 A1 | 9/2011 | Yan |
| 2011/0250875 A1 | 10/2011 | Huang et al. |
| 2011/0255454 A1 | 10/2011 | Hauser et al. |
| 2011/0263331 A1 | 10/2011 | Koski et al. |
| 2012/0154115 A1 | 6/2012 | Herrala |
| 2012/0161963 A1 | 6/2012 | Herrala |
| 2012/0218078 A1 | 8/2012 | Hill |
| 2012/0223834 A1 | 9/2012 | Hyatt |
| 2012/0309408 A1 | 12/2012 | Marti et al. |
| 2012/0309422 A1 | 12/2012 | Lewis-Evans et al. |
| 2013/0069782 A1 | 3/2013 | Duggal et al. |
| 2013/0152216 A1 | 6/2013 | Stevens |
| 2013/0159825 A1 | 6/2013 | Nishio et al. |
| 2013/0197859 A1 | 8/2013 | Albano et al. |
| 2014/0006129 A1 | 1/2014 | Heath |
| 2014/0062695 A1 | 3/2014 | Rosen et al. |
| 2014/0073262 A1 | 3/2014 | Gutierrez et al. |
| 2014/0085089 A1 | 3/2014 | Rasband et al. |
| 2014/0162693 A1 | 6/2014 | Wachter et al. |
| 2014/0213301 A1 | 7/2014 | Evans et al. |
| 2014/0274135 A1 | 9/2014 | Edge et al. |
| 2014/0274136 A1 | 9/2014 | Edge et al. |
| 2014/0369695 A1 | 12/2014 | D'Andrade et al. |
| 2015/0006666 A1 | 1/2015 | Backholm et al. |
| 2015/0057518 A1 | 2/2015 | Lebel et al. |
| 2015/0112264 A1 | 4/2015 | Kamen et al. |
| 2015/0160328 A1 | 6/2015 | Peinhardt et al. |
| 2015/0168173 A1 | 6/2015 | Lewis-Evans et al. |
| 2015/0296477 A1 | 10/2015 | Pan et al. |
| 2015/0356862 A1 | 12/2015 | Daoura et al. |
| 2016/0105764 A1 | 4/2016 | Evans et al. |
| 2016/0105765 A1 | 4/2016 | Farley et al. |
| 2017/0164156 A1 | 6/2017 | Evans et al. |
| 2019/0122519 A1 | 4/2019 | Pooya |
| 2020/0402383 A1 | 12/2020 | Pooya |

FOREIGN PATENT DOCUMENTS

| | | |
|---|---|---|
| CN | 102103786 A | 6/2011 |
| KR | 10-2010-0068850 A | 6/2010 |
| WO | 03/60752 A1 | 7/2003 |
| WO | 2014/042407 A1 | 3/2014 |

OTHER PUBLICATIONS

Amended Complaint for Patent Infringement, Exhibit A, dated Oct. 29, 2020, Linquet Technologies, Inc. v. Tile, Inc., Case 3:20-cv-05153-NC, p. 41.

Amended Schuduling Order, dated Aug. 9, 2021, United States District Court Northern District of California, Case No. 3:20-cv-05153-JD, p. 2.

Authorizing Reply to Patent Owner Preliminary Response and Sur-Reply Authorizing Petitioner to File a Corrected Petition 37 C.F.R. §§ 42.5, 42.20, 42.104(c), 42.108©, dated Sep. 17, 2021, Tile, Inc., U.S. Patent and Trademark Office before the Patent Trial and Appeal Board, U.S. Pat. No. 10,163,318, Case No. IPR2021-00927; 5 pages.

Calendar for: Judge James Donato, Linquet Ex. 2005, Tile v. Linquet, IPR2021-00927, Aug. 18, 2021, 8 pages.

Calendar for: Judge James Donato, Tile Exhibit 1044, IPR2021-00927, Tile, Inc. v. Linquet Technologies, Inc., Aug. 24, 2021, 8 pages.

Calendar for: Judge James Donato, Tile Exhibit 1045, IPR2021-00927, Tile, Inc. v. Linquet Technologies, Inc., Sep. 27, 2021, 9 pages.

Carr IV, et al., "How the Pandemic Is Shaping Patent Trials in District Courts," Troutman Pepper Hamilton Sanders LLP., Feb. 18, 2021, p. 9.

Complaint for Patent Infringement, dated Jul. 27, 2020, United States District Court Northern District of California, Case 3:20-cv-05153-NC, p. 10.

Corrected Petition for Inter Partes Review of U.S. Pat. No. 10,163,318, dated Sep. 22, 2021, Tile, Inc., U.S. Patent and Trademark Office before the Patent Trial and Appeal Board, Case No. IPR2021-00927; 114 pages.

Court Order, U.S. District Court, California Northern District, Case Name: Linquet Technologies, Inc. v. Tile, Inc., Case No. 3:20-cv-05153-JD, filed on Jun. 9, 2021, 1 page.

Curriculum Vitae of Daniel Wayne Engels, Ph.D., p. 33.

Declaration of Christopher M. Schmandt, dated May 5, 2021, U.S. Pat. No. 10,163,318, United States Patent and Trademark Office Before the Patent Trial and Appeal Board.

Declaration of Puneet Kohli in Support of Motion for Pro Hac Vice Admission, dated Jul. 9, 2021, Tile, Inc., U.S. Patent and Trademark Office before the Patent Trial and Appeal Board, U.S. Pat. No. 10,163,318, Case No. IPR2021-00927; 4 pages.

Declaration of Reid E. Dodge in Support of Patent Owner'S Preliminary Response, dated Aug. 20, 2021, Tile, Inc., U.S. Patent and Trademark Office before the Patent Trial and Appeal Board, U.S. Pat. No. 10,163,318, Case No. IPR2021-00927; 3 pages.

Declaration of Sarah J. Guske in Support of Motion for Pro Hac Vice Admission, dated Jul. 9, 2021, Tile, Inc., U.S. Patent and Trademark Office before the Patent Trial and Appeal Board, U.S. Pat. No. 10,163,318, Case No. IPR2021-00927; 4 pages.

Defendant Tile, Inc.'s Invalidity Contentions Pursuant To Patent Local Rules 3-3 and 3-4, dated Feb. 9, 2021, United States District Court Northern District of California, Case No. 3:20-cv-05153-JD, p. 127.

Deposition of Christopher Schmandt Via Zoom from Winchester, MA, dated Feb. 1, 2022, Tile, Inc., U.S. Patent and Trademark Office before the Patent Trial and Appeal Board, U.S. Pat. No. 10,163,318, Case No. IPR2021-00927; 136 pages.

Email from Sarah Guske to Board, IPR2021-00927: Tile v. Linquet, Sep. 3, 2021, 2 pages.

Expert Declaration of Daniel W. Engels, Ph.D., dated Aug. 20, 2021, Tile, Inc., U.S. Patent and Trademark Office before the Patent Trial and Appeal Board, U.S. Pat. No. 10,163,318, Case No. IPR2021-00927; 53 pages.

General Order No. 72-5: Coronavirus Disease Public Health Emergency, United States District Court Northern District of California, Jul. 23, 2020, p. 2.

Granting Institution of Inter Partes Review 35 U.S.C. § 314, dated Nov. 17, 2021, Tile, Inc., U.S. Patent and Trademark Office before the Patent Trial and Appeal Board, U.S. Pat. No. 10,163,318, Case No. IPR2021-00927; 48 pages.

(56) References Cited

OTHER PUBLICATIONS

Granting Petitioner's Motions for Pro Hac Vice Admission of Sarah J. Guske and Puneet Kohli 37 C.F.R. § 42.10, dated Jul. 28, 2021, Tile, Inc., U.S. Patent and Trademark Office before the Patent Trial and Appeal Board, U.S. Pat. No. 10,163,318, Case No. IPR2021-00927; 3 pages.
Joint Claim Construction and Prehearing Statement, dated Apr. 5, 2021, United States District Court Northern District of California, Case No. 3:20-cv-05153-JD, p. 7.
Joint Stipulation and Motion To Amend/Correct Scheduling Order, dated Mar. 23, 2021, United States District Court Northern District of California, Case No. 3:20-cv-05153-JD, p. 5.
Joint Stipulation To Amend Scheduling Order & [Proposed] Order, dated May 18, 2021, United States District Court Northern District of California, Case No. 3:20-cv-05153-JD, p. 5.
Joint Stipulation To Extend Claim Construction & Motion To Stay Briefing Schedules & [Proposed] Order, dated May 4, 2021, United States District Court Northern District of California, Case No. 3:20-cv-05153-JD, p. 5.
Judge James Donato's Order, *Parus Holdings Inc.* v. *LG Electronics Inc et al.*, U.S. District Court California Northern District (San Francisco) For Case #: 3:20-cv-05896-JD, p. 54.
*Linquet Technologies* v *Tile, Inc.* (Case No. 3:20-cv-05153-JD)—Discovery Meet & Confer, 9 pages.
Linquet Technologies, Inc.'s Infringement Contentions, dated Dec. 28, 2020, United States District Court Northern District of California, Case No. 3:20-cv-05153-JD, p. 71.
Linquet's Infringement Contentions U.S. Pat. No. 10,163,318, Accused Instrumentalities: The Tile System2, p. 66.
Notice of Filing Date Accorded To Petition and Time for Filing Pa Tent Owner Preliminary Response, dated May 21, 2021, Tile, Inc., U.S. Patent and Trademark Office before the Patent Trial and Appeal Board, U.S. Pat. No. 10,163,318, Case No. IPR2021-00927; 5 pages.
Notice of Stipulation Regarding Due Dates 1, 2 and 3, dated Jan. 10, 2022, Tile, Inc., U.S. Patent and Trademark Office before the Patent Trial and Appeal Board, U.S. Pat. No. 10,163,318, Case No. IPR2021-00927; 3 pages.
Order Re Motion To Dismiss, dated Sep. 15, 2021, United States District Court Northern District of California, Case No. 3:20-cv-05153-JD, p. 12.
PacerPro, corresponds to case # 3:20-cv-05153-JD, "*Linquet Technologies, Inc.* v. *Tile, Inc.*.", filed Sep. 17, 2021, 1 page.
Patent Local Rules, United States District Court Northern District of California, USDC Patent Local Rules—Revised Nov. 4, 2020, p. 10.
Patent Owner Preliminary Response, dated Aug. 20, 2021, Tile, Inc., U.S. Patent and Trademark Office before the Patent Trial and Appeal Board, U.S. Pat. No. 10,163,318, Case No. IPR2021-00927; 54 pages.
Patent Owner's Request for Oral Argumentpursuant To 37 C.F.R. §42.70(a), dated Jul. 6, 2022, Tile, Inc., U.S. Patent and Trademark Office before the Patent Trial and Appeal Board, U.S. Pat. No. 10,163,318, Case No. IPR2021-00927; 4 pages.
Patent Owner's Additional Power of Attorney Pursuant To 37 C.F.R. § 42.10(b), dated May 28, 2021, Tile, Inc., U.S. Patent and Trademark Office before the Patent Trial and Appeal Board, U.S. Pat. No. 10,163,318, Case No. IPR2021-00927; 2 pages.
Patent Owner's Authorized Surreply, dated Oct. 7, 2021, Tile, Inc., U.S. Patent and Trademark Office before the Patent Trial and Appeal Board, U.S. Pat. No. 10,163,318, Case No. IPR2021-00927; 7 pages.
Patent Owner's Exhibit List, dated Aug. 20, 2021, Tile, Inc., U.S. Patent and Trademark Office before the Patent Trial and Appeal Board, U.S. Pat. No. 10,163,318, Case No. IPR2021-00927; 3 pages.
Patent Owner's Exhibit List, dated Feb. 23, 2022, Tile, Inc., U.S. Patent and Trademark Office before the Patent Trial and Appeal Board, U.S. Pat. No. 10,163,318, Case No. IPR2021-00927; 3 pages.
Patent Owner's Mandatory Notices Pursuant To 37 C.F.R. §42.8(a)(2) and (b), dated Jun. 2, 2021, Tile, Inc., U.S. Patent and Trademark Office before the Patent Trial and Appeal Board, U.S. Pat. No. 10,163,318, Case No. IPR2021-00927; 4 pages.
Patent Owner's Notice of Deposition of Christopher M. Schmandt, dated Jan. 10, 2022, Tile, Inc., U.S. Patent and Trademark Office before the Patent Trial and Appeal Board, U.S. Pat. No. 10,163,318, Case No. IPR2021-00927; 3 pages.
Patent Owner's Response, dated Feb. 23, 2022, Tile, Inc., U.S. Patent and Trademark Office before the Patent Trial and Appeal Board, U.S. Pat. No. 10,163,318, Case No. IPR2021-00927; 52 pages.
Patent Owner's Sur-Reply, dated Jun. 29, 2022, Tile, Inc., U.S. Patent and Trademark Office before the Patent Trial and Appeal Board, U.S. Pat. No. 10,163,318, Case No. IPR2021-00927; 30 pages.
Patent Owner's Updated Mandatory Notices Pursuant To 37 C.F.R. §42.8(a)(2) AND (b), dated Apr. 1, 2022, Tile, Inc., U.S. Patent and Trademark Office before the Patent Trial and Appeal Board, U.S. Pat. No. 10,163,318, Case No. IPR2021-00927; 3 pages.
Petition for Inter Partes Review of U.S. Pat. No. 10,163,318, dated May 13, 2021, Tile, Inc., U.S. Patent and Trademark Office before the Patent Trial and Appeal Board; 114 pages.
Petition for Inter Partes Review of U.S. Pat. No. 10,163,318, dated May 14, 2021, Tile, Inc., U.S. Patent and Trademark Office before the Patent Trial and Appeal Board, Case No. IPR2021-00927; 2 pages.
Petitioner's Reply To Patent Owner's Reponse, dated May 18, 2022, Tile, Inc., U.S. Patent and Trademark Office before the Patent Trial and Appeal Board, U.S. Pat. No. 10,163,318, Case No. IPR2021-00927 34 pages.
Petitioner's Request for Oral Hearing 37 C.F.R. §42.70, dated Jul. 5, 2022, Tile, Inc., U.S. Patent and Trademark Office before the Patent Trial and Appeal Board, U.S. Pat. No. 10,163,318, Case No. IPR2021-00927; 4 pages.
Petitioner's Authorized Reply To Patent Owner'S Preliminary Response, dated Sep. 27, 2021, Tile, Inc., U.S. Patent and Trademark Office before the Patent Trial and Appeal Board, U.S. Pat. No. 10,163,318, Case No. IPR2021-00927; 10 pages.
Petitioner's Motion for Pro Hac Vice Admission of Puneet Kohli, dated Jul. 9, 2021, Tile, Inc., U.S. Patent and Trademark Office before the Patent Trial and Appeal Board, U.S. Pat. No. 10,163,318, Case No. IPR2021-00927; 11 pages.
Petitioner's Motion for Pro Hac Vice Admission of Sarah J. Guske, dated Jul. 9, 2021, Tile, Inc., U.S. Patent and Trademark Office before the Patent Trial and Appeal Board, U.S. Pat. No. 10,163,318, Case No. IPR2021-00927; 5 pages.
Petitioner's Objections To Patent Owner's Evidence Pursuant To 37 C.F.R. § 42.64(b)(1), dated Mar. 2, 2022, Tile, Inc., U.S. Patent and Trademark Office before the Patent Trial and Appeal Board, U.S. Pat. No. 10,163,318, Case No. IPR2021-00927; 3 pages.
Petitioner's Updated Exhibit List, dated Aug. 20, 2021, Tile, Inc., U.S. Patent and Trademark Office before the Patent Trial and Appeal Board, U.S. Pat. No. 10,163,318, Case No. IPR2021-00927; 6 pages.
Petitioner's Updated Exhibit List, dated Aug. 23, 2021, Tile, Inc., U.S. Patent and Trademark Office before the Patent Trial and Appeal Board, U.S. Pat. No. 10,163,318, Case No. IPR2021-00927; 6 pages.
Petitioner's Updated Exhibit List, Dated Jun. 25, 2021, Tile, Inc., U.S. Patent and Trademark Office before the Patent Trial and Appeal Board, U.S. Pat. No. 10,163,318, Case No. IPR2021-00927; 5 pages.
Petitioner's Updated Exhibit List, dated Sep. 17, 2021, Tile, Inc., U.S. Patent and Trademark Office before the Patent Trial and Appeal Board, U.S. Pat. No. 10,163,318, Case No. IPR2021-00927; 6 pages.
Petitioner's Updated Mandatory Notices Under 37 C.F.R. § 42.8(?)(3), dated Aug. 20, 2021, Tile, Inc., U.S. Patent and Trademark Office before the Patent Trial and Appeal Board, U.S. Pat. No. 10,163,318, Case No. IPR2021-00927; 3 pages.
Petitioner's Updated Mandatory Notices Under 37 C.F.R. § 42.8(?)(3), Dated Aug. 23, 2021, Tile, Inc., U.S. Patent and Trade-

(56) References Cited

OTHER PUBLICATIONS mark Office before the Patent Trial and Appeal Board, U.S. Pat. No. 10,163,318, Case No. IPR2021-00927; 3 pages.
Petitioner's Updated Mandatory Notices Under 37 C.F.R. § 42.8(?)(3), dated Jun. 25, 2021, Tile, Inc., U.S. Patent and Trademark Office before the Patent Trial and Appeal Board, U.S. Pat. No. 10,163,318, Case No. IPR2021-00927; 3 pages.
Petitioner's Updated Mandatory Notices Under 37 C.F.R. § 42.8(?)(3), dated Sep. 17, 2021, Tile, Inc., U.S. Patent and Trademark Office before the Patent Trial and Appeal Board, U.S. Pat. No. 10,163,318, Case No. IPR2021-00927; 3 pages.
Petitioner's Updated Mandatory Notices Under 37 C.F.R. § 42.8(b)(3)(4), dated Jul. 9, 2021, Tile, Inc., U.S. Patent and Trademark Office before the Patent Trial and Appeal Board, U.S. Pat. No. 10,163,318, Case No. IPR2021-00927; 4 pages.
Petitioner's Updated Power of Attorney appointing Kirsten Daru filed with PTAB, dated Jul. 9, 2021, U.S. Pat. No. 10,163,318; 3 pages.
Phero et al., "Success of Motions to Stay Rising, But Why?," Sterne Kessler Goldstein & Fox, 2020, p. 5.
Plaintiff Linquet Technologies, Inc.'s Opposition To Defendant Tile Inc.'s Motion To Dismiss Plaintiff's Amended Complaint, dated Nov. 27, 2020, United States District Court Northern District of California, Case No. 3:20-cv-05153-JD, p. 20.
Plaintiff's Responses To Defendant's First Set of Interrogatories, Mar. 29, 2021, United States District Court Northern District of California, Case No. 3:20-cv-05153-JD, p. 10.
Power of Attorney appointing Kirsten Daru filed with PTAB dated May 12, 2021, U.S. Pat. No. 10,163,318; 3 pages.
Prosecution File History for U.S. Pat. No. 10,163,318, Jun. 11, 2018, 528 pages.
Reporter's Transcript, dated Sep. 8, 2021, Tile, Inc., U.S. Patent and Trademark Office before the Patent Trial and Appeal Board, U.S. Pat. No. 10,163,318, Case No. IPR2021-00927; 4 pages.
Road Show, "Cobra Tag finds your keys, finds your phone (hands-on)" p. 5.
Scarfone, et al., "Guide to Bluetooth Security: Recommendations of the National Institute of Standards and Technology," N.I.S.T., p. 66.
Scheduling Order, dated Feb. 5, 2021, United States District Court Northern District of California, Case No. 3:20-cv-05153-JD, p. 2.
Scheduling Order, dated Nov. 17, 2021, Tile, Inc., U.S. Patent and Trademark Office before the Patent Trial and Appeal Board, U.S. Pat. No. 10,163,318, Case No. IPR2021-00927; 13 pages.
Setting Oral Argument 37 C.F.R. §42.70, dated Jul. 18, 2022, Tile, Inc., U.S. Patent and Trademark Office before the Patent Trial and Appeal Board, U.S. Pat. No. 10,163,318, Case No. IPR2021-00927; 10 pages.
Supplemental Expert Declaration of Daniel W. Engels, Ph.D., dated Feb. 22, 2022, Tile, Inc., U.S. Patent and Trademark Office before the Patent Trial and Appeal Board, U.S. Pat. No. 10,163,318, Case No. IPR2021-00927; 18 pages.

The American Heritage Concise Dictionary, Third Edition, Tile Exhibit 1016, 19 pages.
The Oxford American College Dictionary, Tile Exhibit 1015, 20 pages.
Tile, Inc.'S Stipulation of Invalidity Contentions for U.S. Pat. No. 10,163,318, dated Aug. 12, 2021, United States District Court Northern District of California, Case No. 3:20-cv-05153-JD, p. 4.
U.S. District Court, Civil Docket For Case#3:20-cv-05153-JD, Filed on Jul. 27, 2020, 8 pages.
Wavetren D, "ActivDuo Mini Asset Tag: TG1810-A" Active Rfid, Feb. 2009, p. 2.
"Linquet-Linking Everything" video available at http://www.youtube.com/watch?v=6NNGGfEd3dQU, last accessed Dec. 21, 2011, dated as uploaded Mar. 18, 2011.
Cao Gadgets LLC. "Monitor and Find Everything in Your Home or Office from the Internet". <http://www.wirelesstag.net/index_ie.html>.
Honig, Zack StickNFind Bluetooth stickers let you tag and locate your goods with a smartphone (hands-on-video) Jan. 2, 2013. <https://www.engadget.com/2013/01/02/sticknfind-bluetooth-stickers-han- ds-on/>.
International Preliminary Reporton Patentability received for PCT Patent Application No. PCT/IB2013/000489, dated Sep. 18, 2014, 8 pages.
International Search Report and Written Opinion received for PCT Patent Application No. PCT/IB2013/000489, dated Jul. 11, 2013, 9 pages.
Lee, et al., System Architecture Directions for Tangible Cloud Computing, 5 pgs.
Machine translation of CN101883259, published Nov. 10, 2010, 22 pages.
Machine translation of CN101930066, published Dec. 29, 2010, 18 pages.
MSHA, MSHA Approves ActiveMine's RFID Wi-Fi Tags, Active Control Technology, Inc., http://www.morerfid.com/details.php?subdetail=Report&action=details&repor-t.sub.-id=5009&display=RFID, Sep. 26, 2008, 2 pgs.
Notification of Second Office Action and Search Report. State Intellectual Property Office of People's Republic of China, Application No. 201380024290.7 in the name of Linquet Technologies, Inc., dated Jul. 14, 2016, 34 pages.
Office Action and translation dated Aug. 15, 2017 in Chinese Application No. 201380024290.7. 37 pages.
Office Action and translation dated Dec. 20, 2016 in corresponding Chinese Application No. 201380024290.7.
Office Action and translation dated Nov. 24, 2015 in Chinese Application No. 201380024290.7. 30 pages.
RFID Channels, rfid ready, Modular RFID Systems, http://www.rfid-ready.com/200904082772/aruba-networks-rtls-lower-costs-by- -leveraging . . . , Dec. 25, 2011, 3 pgs.

* cited by examiner

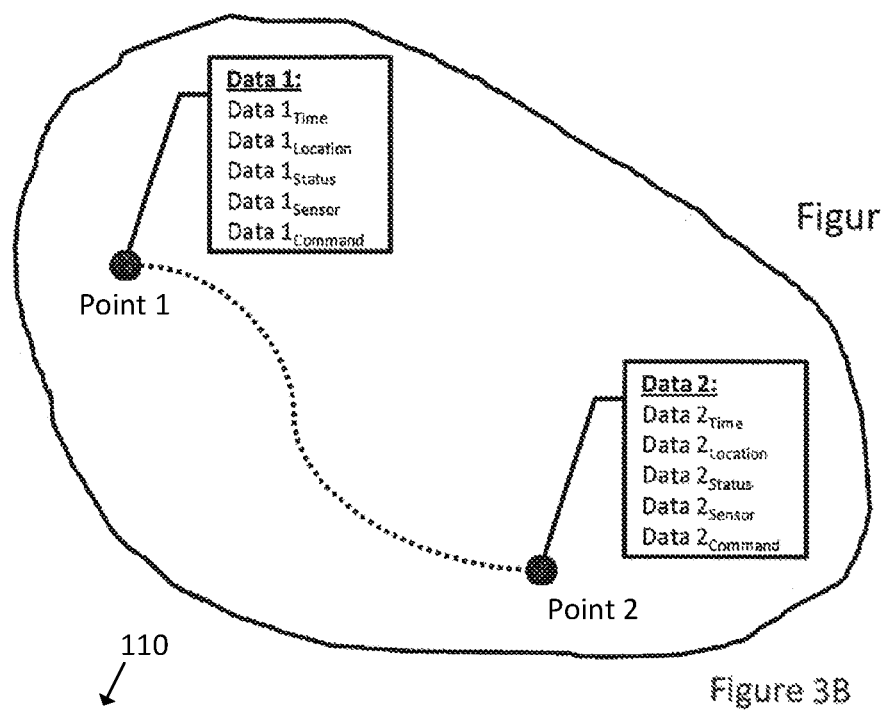

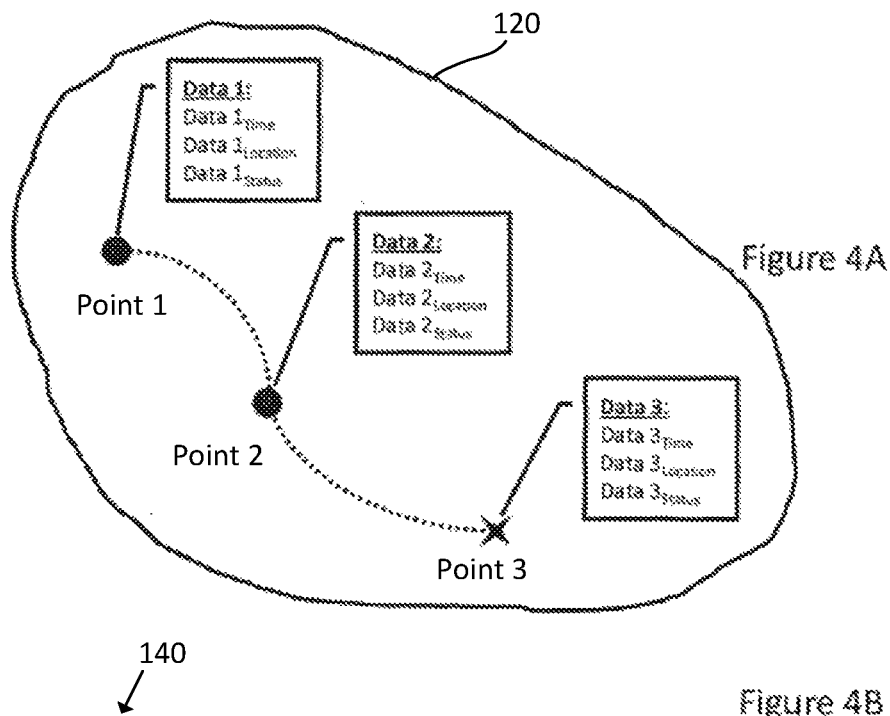

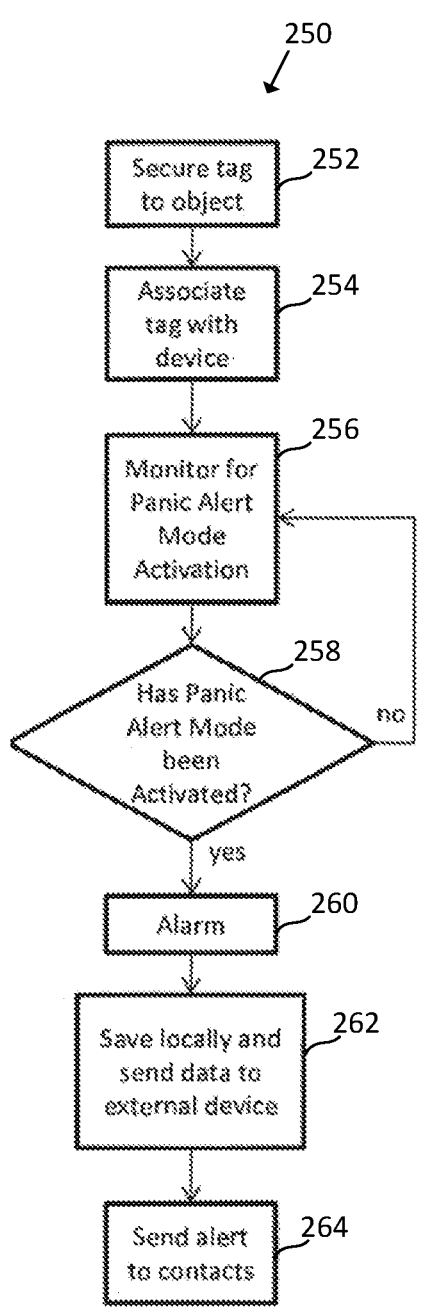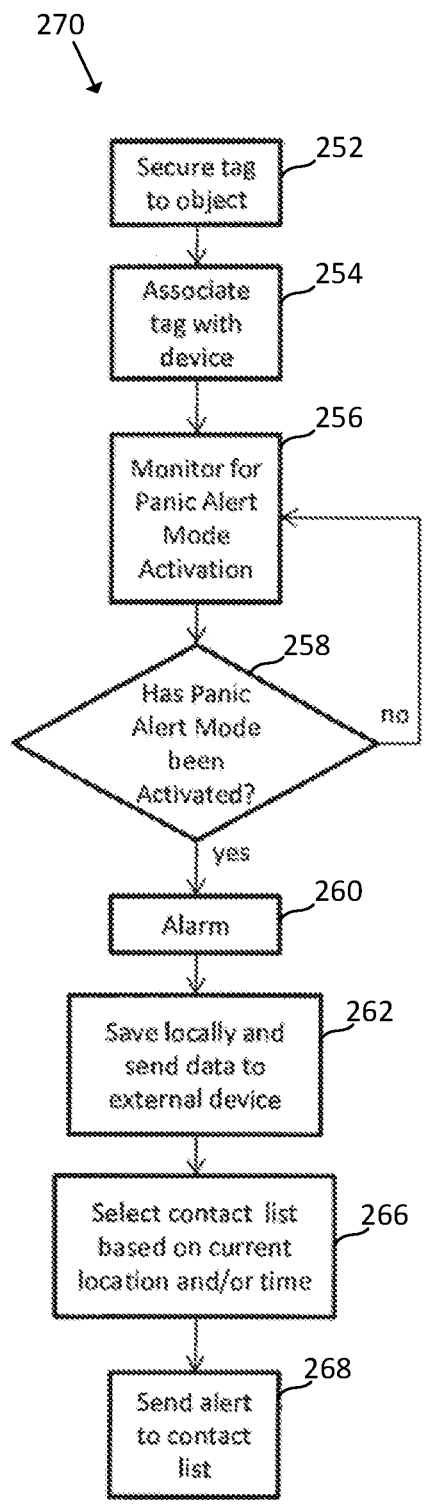
Figure 7A
Figure 7B

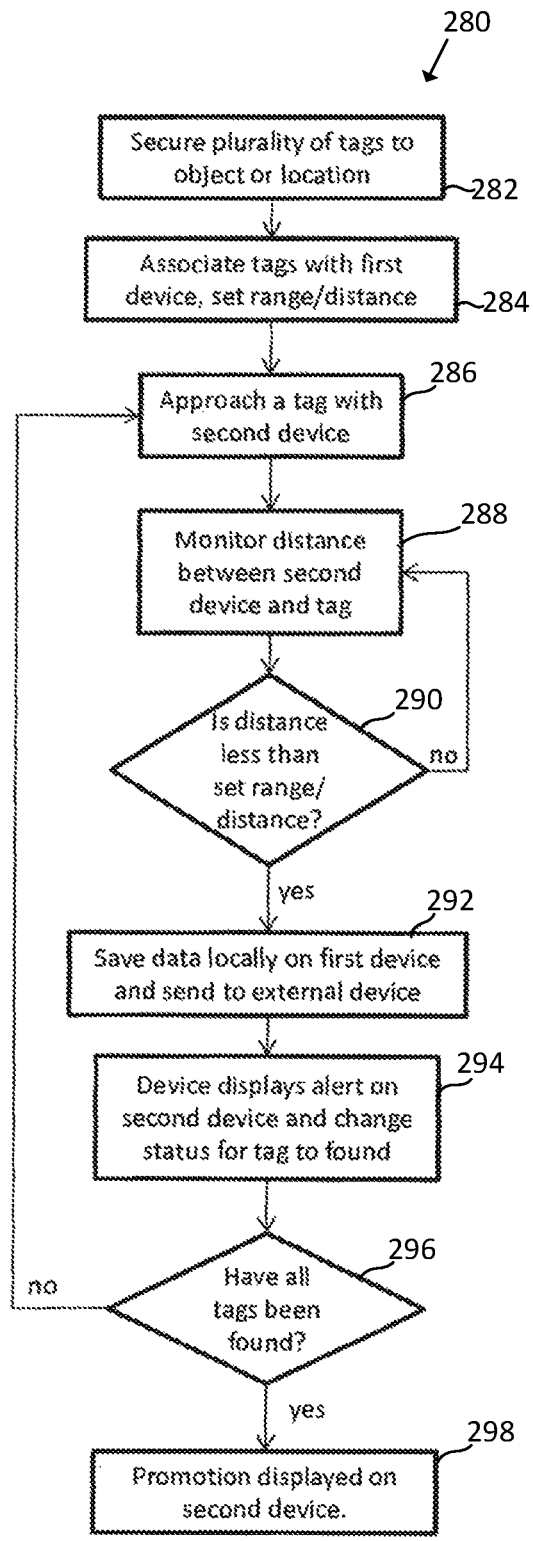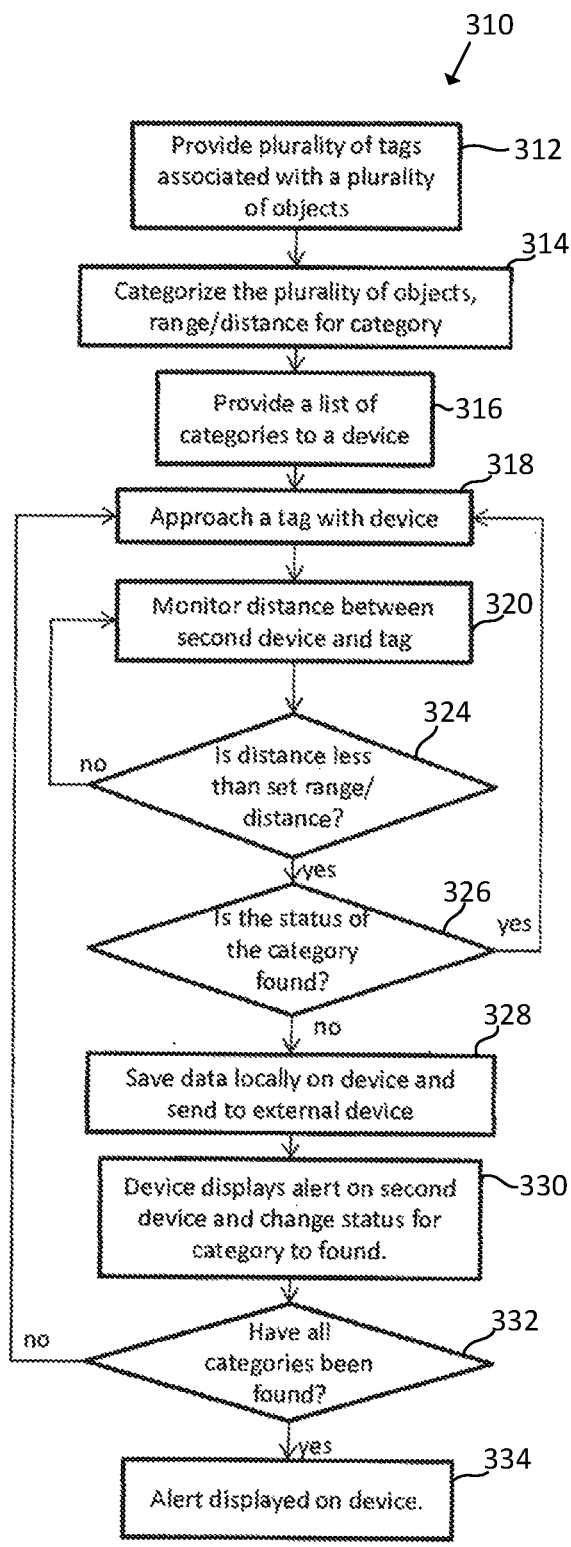
Figure 8A
Figure 8B

| Table | | | | |
|---|---|---|---|---|
| Tag ID | Time left Device 1 range | Time entered Device 2 range | Time left Device 2 range | Time entered Device 3 range |
| Tag 1 | Tag 1 $_{Time\ Out\ 1}$ | Tag 1 $_{Time\ In\ 2}$ | Tag 1 $_{Time\ Out\ 2}$ | Tag 1 $_{Time\ In\ 3}$ |
| Tag 2 | Tag 2 $_{Time\ Out\ 1}$ | Tag 2 $_{Time\ In\ 2}$ | Tag 2 $_{Time\ Out\ 2}$ | Tag 2 $_{Time\ In\ 3}$ |
| Tag 3 | Tag 3 $_{Time\ Out\ 1}$ | Tag 3 $_{Time\ In\ 2}$ | Tag 3 $_{Time\ Out\ 2}$ | Tag 3 $_{Time\ In\ 3}$ |

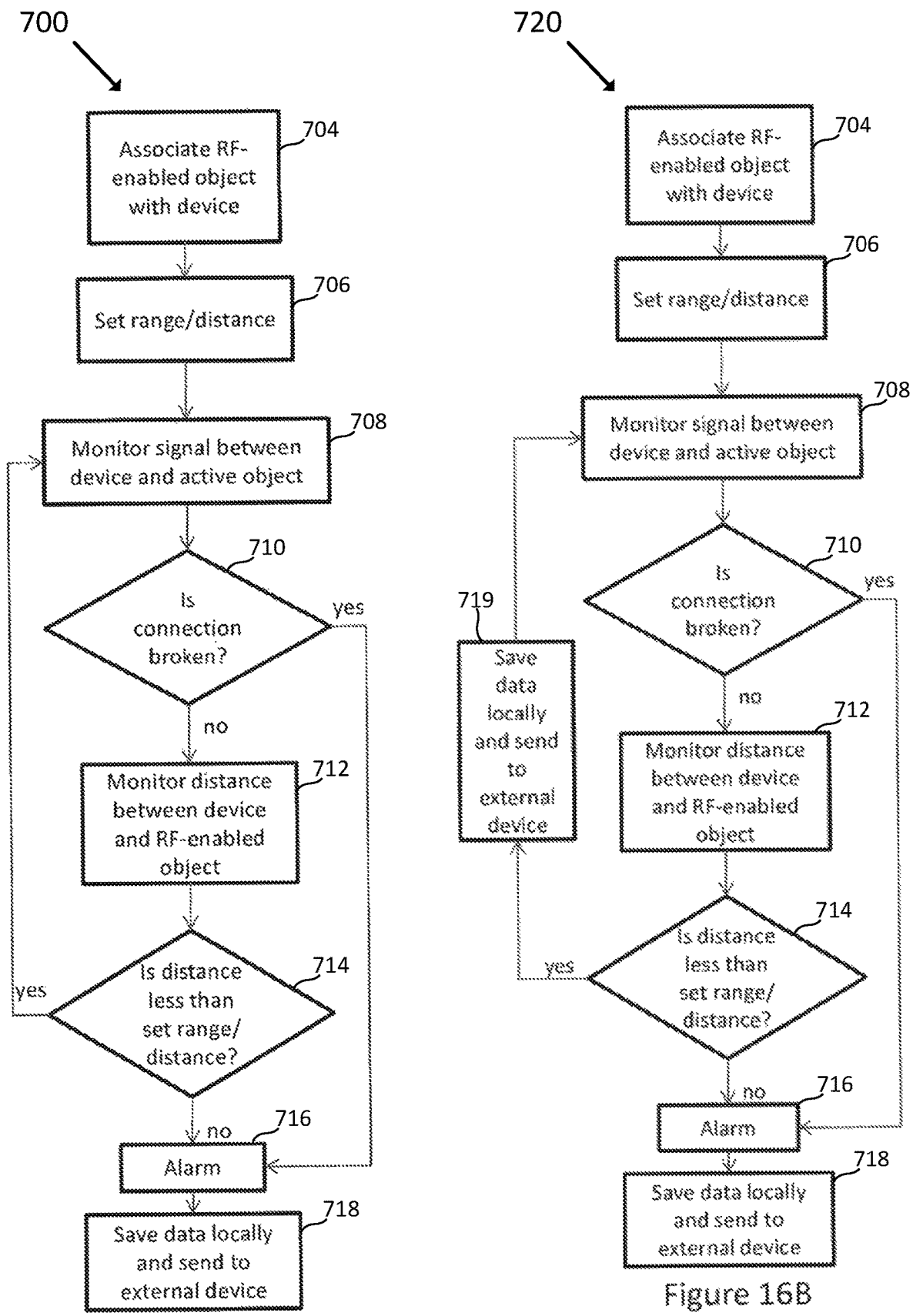

COMPREHENSIVE SYSTEM AND METHOD OF UNIVERSAL REAL-TIME LINKING OF REAL OBJECTS TO A MACHINE, NETWORK, INTERNET, OR SOFTWARE SERVICE

CROSS-REFERENCE TO RELATED APPLICATIONS

This application is a continuation of application Ser. No. 17/014,895, filed Sep. 8, 2020, which is a continuation of application Ser. No. 16/227,572, filed Dec. 20, 2018, now U.S. Pat. No. 10,769,924, which is a continuation of application Ser. No. 16/005,193, filed Jun. 11, 2018, now U.S. Pat. No. 10,163,318, which is a continuation of application Ser. No. 15/156,726, filed May 17, 2016, now U.S. Pat. No. 9,997,043, which is a continuation of application Ser. No. 14/617,240, filed Feb. 9, 2015, now U.S. Pat. No. 9,366,746, which is a continuation application of U.S. patent application Ser. No. 13/754,607, filed Jan. 30, 2013, now U.S. Pat. No. 8,981,938, which claims the benefit under 35 U.S.C. § 119(e) of U.S. Provisional Patent Application Ser. No. 61/608,429 filed Mar. 8, 2012. The disclosures of each of these applications are hereby incorporated by reference in their entireties.

FIELD OF THE DISCLOSURE

The disclosure relates to a method of bidirectional linking, connecting, communicating, and tracking objects, and in particular to a method of tracking the position and status of objects using a wireless tag associated with the object and/or an RF-enabled object.

BACKGROUND AND SUMMARY OF THE DISCLOSURE

A wireless tag to be associated with the object to be linked, tracked, or both is disclosed along with an electronic device for communicating with the tag and updating the information to an external device, such as a computer, network, or the cloud. Information such as, but not limited to time, position (including latitude, longitude, and altitude), speed, direction, temperature, and identification can be transmitted for either real-time linking/tracking and analysis, or a historical view. In one embodiment, the electronic device for communicating with the tag is a cellular phone, a tablet computer, a laptop computer, a pair of electronic glasses, or a watch.

In a first exemplary embodiment, a wireless tag for determining the position of an attached physical object or status of an environment in which the tag is placed is disclosed. In one embodiment, the wireless tag includes a power source for providing electrical power to the wireless tag, a radio transmitter and receiver system for wirelessly exchanging data and command with an electronic device, and a user interface including at least one input and at least one output, wherein the electronic device determines the location or status of the electronic device and a status of whether the distance between the electronic device and wireless tag exceeds a predetermined distance and wirelessly communicates data including the time, the location of the electronic device (including latitude, longitude, and altitude), speed and the status. In another embodiment, the electronic device communicates data to the network at predetermined period intervals and/or upon the initiation of a predetermined event. In still another embodiment, the wireless tag has a thickness of about 10 mm or less, and in another embodiment about 6 mm or less. In yet another embodiment, the communication between the tag and electronic device is encrypted. In yet still another embodiment the wireless tag includes one or more sensors having an output reading. In another embodiment, a plurality of tags is provided.

In a second exemplary embodiment a system for tracking the position of an object is disclosed. In one embodiment, the system includes a wireless tag including a first radio transmitter and receiver system and a user interface including at least one input and at least one output; an electronic device includes a second radio transmitter and receiver system in communication with the first radio transmitter and receiver system, a user interface including at least one output, a module for determining the position of the electronic device, a module for determining the distance or proximity and/or direction of the tag from the device and also for determining a status of whether the distance between the electronic device and wireless tag exceeds a predetermined distance, and a data transmitter for transmitting commands and data including the position of the electronic device and status of the distance between the electronic device and wireless tag; and an external device receiving the data transmitted by the data transmitter and storing the data in a computer readable storage medium. In another embodiment, the system includes a second (3rd, 4th, . . . , nth) wireless tag secured to a second (3rd, 4th, . . . , nth) object to be linked or tracked, the second wireless tag including a third radio transmitter and receiver system; and a user interface including at least one input and one output; wherein the second radio transmitter and receiver system is in communication with the third radio transmitter and receiver system, the electronic device includes a module for determining the distance or proximity and/or direction of the tag from the phone and also for determining a second status of whether the distance between the electronic device and second wireless tag exceeds a second predetermined distance, and the data transmitter for transmits data including the second status.

In a third exemplary embodiment, a method for monitoring the location of an object is disclosed. In one embodiment, the method includes securing a wireless tag to the object, wherein the wireless tag includes a first radio transmitter and receiver system for transmitting and receiving a radio frequency signal; providing a first identification for the wireless tag; associating the wireless tag with an electronic device, wherein the electronic device includes a second radio transmitter and receiver system for transmitting and receiving a radio frequency signal and the electronic device is capable of determining the position of the electronic device; determining the position of the electronic device; providing a second identification for the electronic device; receiving with the second radio transmitter and receiver system the radio frequency signal from first radio transmitter and receiver system; determining with the electronic device the distance or proximity and/or direction of the tag from the phone and also a status of whether the distance between the wireless tag and the electronic device exceeds a predetermined distance based at least in part on the strength or absence of the radio frequency signal; and transmitting data including the first identification, the second identification, the time, the speed, the position of the electronic device, and the status to an external device. In another embodiment, the radio transmitter and receiver systems are Bluetooth transceivers and the tag has a thickness of about 10 mm or less or about 6 mm or less. In still another embodiment, the wireless tag includes an alarm and the second Bluetooth transceiver sends a signal to the first Bluetooth transceiver to activate the alarm or carry out any other predetermined action or command when the status changes because the predetermined distance was exceeded. Alarming or carrying out other actions or commands, could also be initiated by the user, by demand, from any part of the overall system (tag, phone, cloud).

In a fourth exemplary embodiment, a method of preventing the loss and/or theft of an object is disclosed. In one embodiment, the method includes attaching a wireless tag to the object, the wireless tag including a first radio transceiver for transmitting and receiving a radio frequency signal and a tag alarm; associating the wireless tag with an electronic device, the electronic device including a second radio transceiver for transmitting and receiving a radio frequency signal and a device alarm, wherein the electronic device is capable of determining the position of the electronic device; providing an allowable distance or range; monitoring the radio frequency signal from the first radio transceiver received by the second radio transceiver and activating the device alarm if the radio frequency signal is broken; monitoring the radio frequency signal from the second radio transceiver received by the first radio transceiver and activating the tag alarm as well as an alarm (or other outputs like light) on the electronic device if the radio frequency signal is broken; and determining with the electronic device a status of whether the distance between the wireless tag and the electronic device exceeds the allowable distance or range based at least in part on the strength or absence of the radio frequency signal; wherein the electronic device activates at least one of the tag alarm and device alarm, determines the position of the electronic device and saves them on the device and wirelessly transmits data including the time, the speed and the position of the electronic device to an external device if the distance exceeds the allowable distance or range. In another embodiment, the method includes wirelessly transmitting data and commands to the external device including the time and position of the electronic device each time the determining step is performed or by demand.

In a fifth exemplary embodiment, a method of initiating commands is disclosed. In one embodiment, the method includes providing a wireless tag including a first radio transceiver for transmitting and receiving a radio frequency signal and a tag alarm; associating the wireless tag with an electronic device, the electronic device including a second radio transceiver for transmitting and receiving a radio frequency signal and a device alarm, wherein the electronic device is capable of determining the position of the electronic device; providing a predetermined action(s) to be taken upon receiving a predetermined radio frequency signal (or a combination of signals); transmitting the predetermined radio frequency signal from one of the first radio transceiver and second radio transceiver; receiving the predetermined radio frequency signal with the other of the first radio transceiver and second radio transceiver; and taking the predetermined action. In another embodiment, the method is directed to locating an object by sounding an alarm attached to the object or similarly locating the electronic device by activating its alarm (or triggering other output methods).

In a sixth exemplary embodiment, a method of providing a panic alert is disclosed. in one embodiment, the method includes providing a wireless tag including a first radio transceiver for transmitting and receiving a radio frequency signal and a tag alarm; associating the wireless tag with an electronic device, the electronic device including a second radio transceiver for transmitting and receiving a radio frequency signal, and a device alarm, wherein the electronic device is capable of determining the position of the electronic device; transmitting a predetermined radio frequency signal from one of the first and second radio transceivers; receiving the predetermined radio frequency signal with the other of the first and second radio transceivers; activating the tag alarm and device alarm; determining the position of the electronic device; transmitting data including the time, the speed and the position of the electronic device to an external device, carrying out commands/actions on the device and sending commands to the network/cloud; and transmitting data including the time and the position of the electronic device to a predetermined contact(s). In another embodiment, the predetermined contact selected from a list of contacts based at least in part on the position of the electronic device.

In a seventh exemplary embodiment, a method of utilizing a series of wireless tags in a promotion, advertising, education, training or gaming embodiment is disclosed. In one embodiment, the method includes providing a plurality of tags, each tag including a tag radio transceiver for transmitting and receiving a radio frequency signal; providing an allowable distance or range and unique identification for each of the plurality of tags; associating each of the plurality of tags with a first electronic device, the first electronic device including a radio transceiver for communicating with the tag radio transceiver; spacing apart the plurality of tags; approaching a first of the plurality of tags with a second electronic device, the second electronic device including a radio transceiver for communicating with the tag radio transceiver and a user interface; determining with the second electronic device a status of whether the distance between the wireless tag and the electronic device is less than the allowable distance or range based at least in part on the strength or absence of the radio frequency signal; providing an alert on the user interface and transmitting with the second electronic device data including the time and tag identification to an external device if the determining step determines that the distance between the wireless tag and the electronic device is less than the allowable distance or range. In another embodiment, the method includes providing a category for each of the plurality of tags and transmitting the category to the external device if the determining step determines that the distance between the wireless tag and the electronic device is less than the allowable distance or range.

In an eight exemplary embodiment, a method of monitoring a patient in a health care facility is disclosed. In one embodiment, the method includes attaching a wireless tag to the patient, the wireless tag including a first radio transceiver for transmitting and receiving a radio frequency signal and a tag alarm; associating the wireless tag with an electronic device, the electronic device including a second radio transceiver for transmitting and receiving a radio frequency signal and a device alarm, wherein the electronic device is capable of determining the position of the electronic device; providing an allowable distance or range; monitoring the radio frequency signal from the first radio transceiver received by the second radio transceiver and activating the device alarm if the radio frequency signal is broken; monitoring the radio frequency signal from the second radio transceiver received by the first radio transceiver and activating the tag alarm if the radio frequency signal is broken; and determining with the electronic device a status of whether the distance between the wireless tag and the electronic device exceeds the allowable distance or range based at least in part on the strength or absence of the radio frequency signal; wherein the electronic device activates at least one of the tag alarm and device alarm, determines the position of the electronic device and wirelessly transmits data including the time, the temperature, and the position of the electronic device to an external device if the distance exceeds the allowable distance or range. In another embodiment, the method includes saving locally (on the device) and wirelessly transmitting data to the external device including the time and position and speed of the electronic device each time the determining step is performed.

In a ninth exemplary embodiment, a method of monitoring the position of a participant in an athletic event is disclosed. In one embodiment, the method includes securing a wireless tag to the participant, wherein the wireless tag includes a first radio transceiver for transmitting and receiving a radio frequency signal; providing a first identification for the wireless tag; associating the wireless tag with a plurality of electronic devices, wherein each of the electronic devices includes a clock, and a device radio transceiver for transmitting and receiving a radio frequency signal; and providing an identification and a predetermined distance or range for each of the electronic devices; wherein, for each electronic device, determining with the electronic device a status of whether the distance between the wireless tag and the electronic device is less than the predetermined distance based at least in part on the strength or absence of the radio frequency signal and transmitting to an external device the electronic device identification, the time, and the status of whether the distance between the wireless tag and the electronic device is less or more than the predetermined distance In another embodiment, the wireless tag includes an alarm and the device radio transceiver sends a signal to the wireless tag to activate the alarm or carrying out other commands/actions on the device and sending commands to the external device if the distance between the wireless tag and the electronic device is less than the predetermined distance. In another embodiment, the speed of the participant between two points is communicated to an external device.

In a tenth exemplary embodiment, a system for providing an application programming interface (API) and/or software development kit (SDK) is disclosed. In one embodiment, the system includes a wireless tag having a unique identification and including a power source for providing electrical power to the wireless tag, a radio transceiver for wirelessly exchanging potentially encrypted data with an electronic device, and a user interface including at least one input and at least one output wherein the electronic device determines time, the speed and the position of the electronic device and a status of whether the distance between the electronic device and wireless tag exceeds a predetermined distance and wirelessly communicates data and/or commands including the position of the electronic device, time, speed and the status; an electronic device including a radio transceiver capable of communicating with the wireless tag radio transceiver, a user interface including at least one input and one output, a module for determining the position of the electronic device, a module for determining a status of whether the distance between the electronic device and wireless tag exceeds a predetermined distance, and a data transmitter for transmitting data including time, speed and the position of the electronic device and status of the distance between the electronic device and wireless tag to an external device for storage in a computer readable storage medium; an external device in communication with the electronic device and wireless tag and storing data in a computer readable storage medium transmitted by at least one of the wireless tag and electronic device; a computer system executing an application programming interface and/or software development kit in communication with the external device and electronic device, wherein the application programming interface and/or software development kit provides a user interface to one of the external device and electronic device including an input to execute one or more commands transmitted by radio frequency signal to the wireless tag.

In an eleventh exemplary embodiment, a method of providing a positioning service to a customer is disclosed. In one embodiment, the method includes providing a plurality of wireless tags to the customer for small or no charge, each tag having a unique identification and including a power source for providing electrical power to the wireless tag, a radio transceiver for wirelessly exchanging encrypted data with an electronic device, and a user interface including at least one input and at least one output wherein the electronic device determines the position of the electronic device and a status of whether the distance between the electronic device and wireless tag exceeds one or more predetermined distances and wirelessly communicates data including the position, with time and speed of the electronic device and the status; providing a computer-readable medium containing an application programming interface and/or software development kit to the customer and/or a developer, the application programming interface and/or software development kit being configured to support a software application on the tag and/or the electronic device and/or the cloud, wherein the electronic device includes a radio transceiver capable of communicating with the wireless tag radio transceiver, a user interface including at least one input and one output, a module for determining the position, the speed and time of the electronic device, a module for determining a status of whether the distance between the electronic device and wireless tag exceeds one or more predetermined distance, and a data transmitter for transmitting data including the position, with time and speed of the electronic device and status of the distance between the electronic device and wireless tag to an external device for storage in a computer readable storage medium and carrying out commands/actions; and associating the plurality of tags with the application programming interface and/or software development kit for a periodic fee or a consumption-based fee, such as based on how many tags being linked, how many times data or commands are communicated or how much data or commands are communicated in a given period. In another embodiment, the method includes developing programs utilizing the application programming interface and/or software development kit and allowing access to the programs for a free or for a fee.

The above mentioned and other features of the invention, and the manner of attaining them, will become more apparent and the invention itself will be better understood by reference to the following description of embodiments of the invention taken in conjunction with the accompanying drawings.

BRIEF DESCRIPTION OF THE SEVERAL VIEWS OF THE DRAWINGS

The disclosure is explained in greater detail below in reference to the figures. In the figures:

FIG. 3 illustrates exemplary data collected by one embodiment of the disclosed system;

FIG. 3A illustrates exemplary data collected by one embodiment of the disclosed system at two positions or times;

FIG. 3B illustrates an exemplary table storing the data collected in FIG. 3A;

FIG. 4 illustrates exemplary data collected by an anti-loss or anti-theft embodiment;

FIG. 4A illustrates exemplary data collected by an anti-loss or anti-theft embodiment of the disclosed system at three positions;

FIG. 4B illustrates a first exemplary table storing the data collected in FIG. 4A;

FIG. 4C illustrates a second exemplary table storing the data collected in FIG. 4A;

FIG. 5 illustrates exemplary processes of the disclosed system in an anti-loss of anti-theft embodiment;

FIG. 7 illustrates exemplary processes of the disclosed system in a panic-alert mode embodiment;

FIG. 7A illustrates exemplary processes of the disclosed system in a panic-alert mode embodiment;

FIG. 7B illustrates exemplary processes of the disclosed system in a panic-alert mode embodiment;

FIG. 8 illustrates exemplary processes of the disclosed system in a marketing embodiment;

FIG. 8A illustrates an exemplary process of the disclosed system in a marketing embodiment;

FIG. 8B illustrates an exemplary process of the disclosed system in a marketing embodiment;

FIG. 9 illustrates exemplary processes of the disclosed system in a health-care embodiment;

FIG. 11 illustrates exemplary data collected by an athletic competition embodiment of the disclosed system;

FIG. 13A illustrates exemplary methods of utilizing a user input included as part of a wireless tag;

FIG. 14 illustrates an anti-theft or anti-loss embodiment of the disclosed system;

FIG. 16 illustrates exemplary processes of the disclosed RF-enabled object system in an anti-loss or anti-theft embodiment;

FIG. 16A illustrates exemplary processes of the disclosed RF-enabled object system in an anti-loss or anti-theft embodiment;

FIG. 16B illustrates exemplary processes of the disclosed RF-enabled object system in an anti-loss or anti-theft embodiment;

FIG. 17A illustrates an anti-theft or anti-loss embodiment of the disclosed RF-enabled object system; and FIG. 17B illustrates an anti-theft or anti-loss embodiment of the disclosed RF-enabled object system.

DETAILED DESCRIPTION OF THE DRAWINGS

The embodiments disclosed below are not intended to be exhaustive or to limit the invention to the precise forms disclosed in the following detailed description. Rather, the embodiments are chosen and described so that others skilled in the art may utilize their teachings. While the present disclosure is primarily directed to a wireless tag apparatus and methods of linking or tracking an object by an associated wireless tag, it should be understood that the features disclosed herein may have relevance to other linking, connecting, communicating, and tracking, mobile device and cloud applications.

Figure 1A:
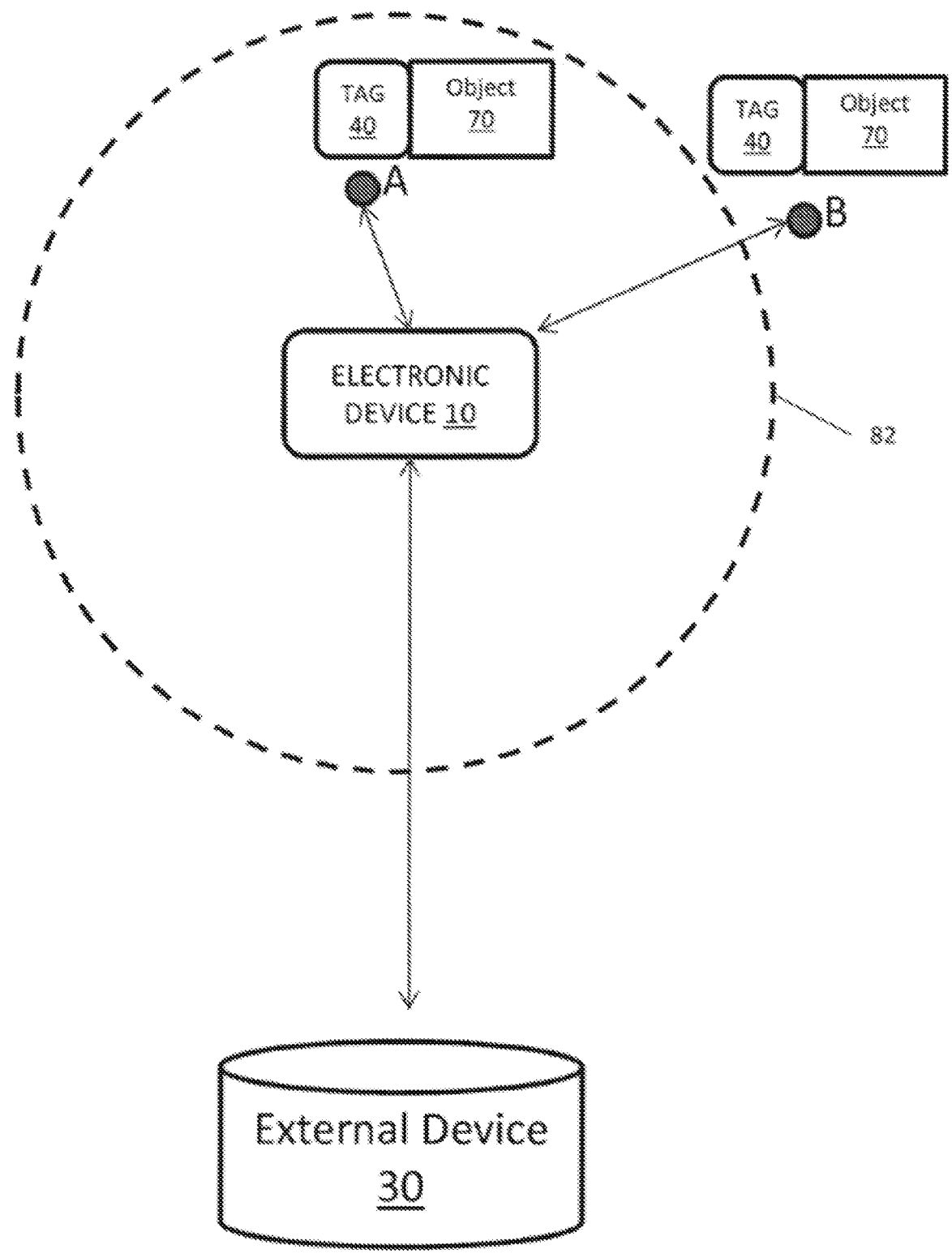
FIG. 1A illustrates an exemplary method of tracking an object attached to a wireless tag according to the present disclosure.

Although a plurality of different embodiments are provided, one exemplary, non-limiting example is illustrated in FIG. 1A. In this exemplary, non-limiting embodiment, an electronic device 10, such as a cellular phone, is provided. Electronic device includes a module determining the current or last known position of electronic device 10. In some embodiments, the current or last position includes one or more of the current or last known altitude, the current or last known latitude and longitude, and the current or last known speed of electronic device 10.

Also shown in the exemplary, non-limiting example illustrated in FIG. 1A, an object 70, such as a wallet is attached to a wireless tag 40. Wireless tag 40 includes a radio transceiver in communication with a radio transceiver included in electronic device 10. Electronic device 10 monitors the strength of the radio signal received from wireless tag 40 to determine the distance between electronic device 10 and wireless tag 40. When the object 70 and tag 40 are within a first distance 82 from electronic device 10, such as at point A, electronic device 10 determines the status of wireless tag 40 to be "in range." When the object 70 and tag 40 are beyond the distance from electronic device 10, such as at point A, electronic device 10 determines the status of wireless tag 40 to be "out of range." When the status of wireless tag 40 change from "in range" to "out of range," either electronic device 10, wireless tag 40, or both alarm.

Also as shown in the exemplary non-limiting example illustrated in FIG. 1A, electronic device periodically sends information relating to its current or last known location and the status of wireless tag 40 to an external device 30, such as an external network or cloud data service. When the status of wireless tag 40 change from "in range" to "out of range," electronic device 10 sends information relating to its current or last known location and the change of status to the external device 30. In this way, a user is given both an alarm when the change in status occurs, as well as a last known location for object 70 based on the strength of the radio signal from tag 40 received by wireless device 10.

Figure 2:
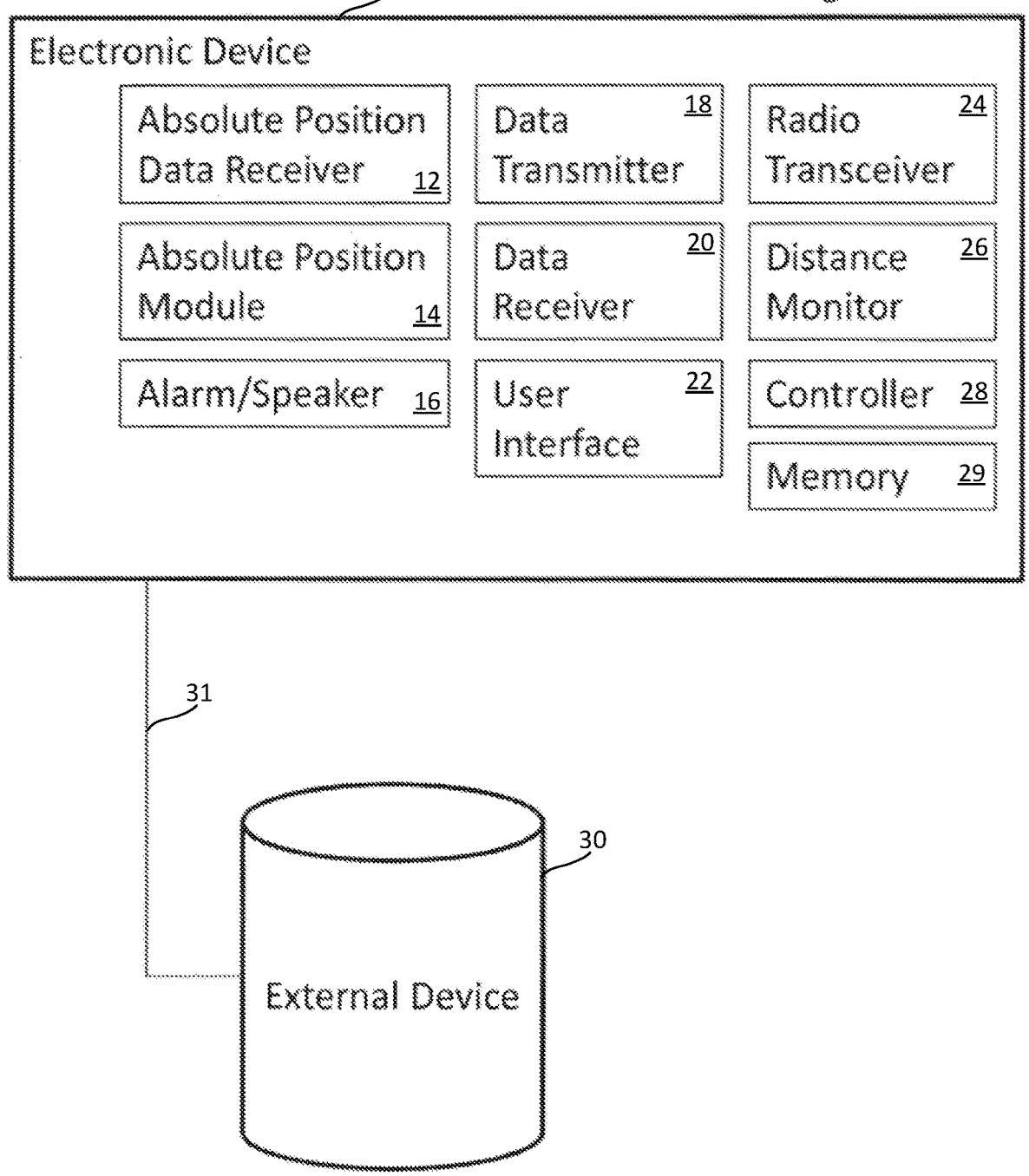
FIG. 2 illustrates an exemplary electronic device and an exemplary external device for use with the wireless tag of FIGS. 1B and 1C.

Referring next to FIG. 2, an exemplary electronic device 10 is illustrated. In one embodiment, electronic device 10 is a cellular phone. In another embodiment, electronic device 10 is a tablet or laptop computer or portable computing device. In still another embodiment, electronic device 10 is an electronic watch or wristband. In yet still another embodiment, electronic device 10 is a portable music player. Other suitable electronic devices, including but not limited to a pair of electronic glasses or sunglasses, may also be used.

In the exemplary embodiment illustrated in FIG. 2, electronic device 10 includes a plurality of hardware and software, including a controller 28. Controller 28 includes logic which may control operating of electronic device 10. The logic of controller 28 may be implemented in hardware or in hardware executing software. Exemplary software may be stored in a memory 29. Memory 29 includes instructions executed by controller 28. Controller 28 may include one or more processors or other structures to implement the logic of controller 28.

Memory is a computer readable medium and may be a single storage device or may include multiple storage devices, located either locally with controller 28 or accessible across a network, or partially locally with controller 28 and partially on external device 30 accessible across a network 31. Computer-readable media may be any available media that may be accessed by controller 28 and includes both volatile and non-volatile media. Further, computer readable-media may be one or both of removable and non-removable media. By way of example, computer-readable media may include, but is not limited to, RAM, ROM, EEPROM, flash memory or other memory technology, CD-ROM, servers, Digital Versatile Disk (DVD) or other optical disk storage, magnetic cassettes, magnetic tape, magnetic disk storage or other magnetic storage devices, or any other medium which may be used to store the desired information and which may be accessed by controller 28. In one embodiment, controller 28 communicates data, status information, or a combination thereof to a remote device for storage, analysis, or carrying out a predetermined command. In another embodiment, memory may further include operating system software. Memory further includes communications software for communication with a network, such as a local area network, a public switched network, a CAN network, and any type of wired or wireless network. An exemplary public switched network is the Internet. Exemplary communications software includes e-mail software, SMS, Bluetooth communication software, radio frequency communication software, near field communication software and internet browser software. Other suitable software which permit controller 28 to communicate with other devices across a network may be used.

As illustrated in FIG. 2, in one embodiment, electronic device 10 further includes user interface 22 comprising one or more I/O modules which provide an interface between an operator or environment or both, and electronic device 10. Exemplary I/O modules include input members and output members. Exemplary input members include buttons, switches, keys, a touch display, a microphone, a camera or other optical reader, a keyboard, a mouse, a transceiver, a sensor, and other suitable devices or methods for providing information to controller. Exemplary output devices include lights, a display (such as a touch screen), printer, vibrator, speaker, visual devices, audio devices including alarm/speaker 16, tactile devices, transceiver, and other suitable devices or methods for presenting information to an operator or a machine.

In one embodiment, electronic device 10 includes absolute position data receiver 12 and absolute position module 14. Absolute position data receiver 12 receives location-based data from external sources. In one exemplary embodiment, absolute position data receiver 12 receives data from a combination of cellular towers, wireless networks including Wi-Fi networks, and global positioning systems (GPS). Absolute position module 14 determines the location of electronic device 10 from the location based data received by absolute position data receiver 12. In another embodiment, absolute position module 14 determines the speed of electronic device 10 from the location based data received by absolute position data receiver 12. In one exemplary embodiment, absolute position data receiver 12 and absolute position module 14 are provided as part of the operating software of electronic device 10. In another exemplary embodiment, absolute position data receiver 12 and/or absolute position module 14 are included on a card, hardware, device or software program in communication with the operating software of electronic device 10.

In another exemplary embodiment, absolute position module 14 determines the latitude and longitude of electronic device 10. In still another exemplary embodiment, absolute position module 14 determines the altitude of electronic device 10. In yet still another exemplary embodiment, absolute position module 14 determines the speed of electronic device 10.

In the exemplary embodiment illustrated in FIG. 2, electronic device 10 includes radio transceiver 24. Radio transceiver 24 sends and receives data to and from other radio transceivers, including radio transceiver 56 incorporated in wireless tag 40. In one embodiment, radio transceiver 24 may comprise a single transceiver. In another embodiment, radio transceiver 24 comprises a separate transmitter and receiver.

In one embodiment, radio transceiver 24 is a Bluetooth (R) transceiver that operates on Bluetooth protocols. As used herein, Bluetooth includes Bluetooth, ULP Bluetooth (Ultra Low Power Bluetooth), BLE (Bluetooth Low Energy), and other standards sets by Bluetooth SIG, Inc. In another embodiment, radio transceiver operates on RF protocols. In still another embodiment, radio transceiver 24 operates on NFC protocols. Other suitable radio transceivers may also be used. In one embodiment, at least some of the data exchanged is encrypted.

Bluetooth connections are relatively power efficient, have relatively little interference issues, are supported by a variety of phone manufacturers and models, and allow bidirectional communication over relatively long ranges. RFID and NFC connections may require less expensive components and may use less power from power supply 60 of wireless tag 40 (see FIG. 1B).

In the exemplary embodiment illustrated in FIG. 2, electronic device 10 includes distance monitor 26. In one embodiment, distance monitor 26 monitors communication between radio transceiver 24 and wireless tag 40. In this embodiment, distance monitor 26 may determine the status of the connection between electronic device 10 and wireless tag 40 to determine if the connection is dropped, broken, lost, or otherwise not present. In another embodiment, distance monitor 26 determines a distance between electronic device 10 and wireless tag 40 based at least in part on the strength of the signal received from wireless tag 40. In still another embodiment, controller 28 may compare the distance determined by distance monitor 26 with a selected distance to alert the user if the determined distance exceeds the selected or predetermined distance. In yet still another embodiment, controller 28 may compare the signal strength with a desired signal strength from a user to alert the user if the signal strength is weaker than the desired signal strength. In another embodiment, controller 28 may compare the distance determined by distance monitor 26 with a predetermined distance or predetermined signal strength, such as but not limited to a received signal strength indicator, corresponding to a user input, such as but not limited to "Close," "Mid," or "Far." In still another embodiment, controller 28 may compare the signal strength with a desired signal strength from a user and alert the user if the signal strength is stronger than the desired signal strength.

In the exemplary embodiment illustrated in FIG. 2, electronic device 10 includes data transmitter 18 and data receiver 20. Data transmitter 18 sends data to external device 30, and data receiver 20 receives data from external device 30. In one exemplary embodiment, radio transceiver 24 also functions as data transmitter 18 and/or data receiver 20. In another exemplary embodiment, data transmitter 18 and data receiver 20 are separate from radio transceiver 24. In one embodiment, data transmitter 18 and data receiver 20 exchange data with external device 30 using Wi-Fi standards, such as the IEEE802.11 family of standards or WiMAX standards, such as IEEE802.16. In another embodiment, data is exchanged using a wide area network standard, including but not limited to, LTE, HPSA, UMTS, GPRS, EDGE, iBurst, EV-DO. In still another embodiment, data is exchanged using a personal area network standard, including, but not limited to Bluetooth, ZigBee, ANT, and Wireless USB. Other suitable mobile data standards may also be used. In another embodiment, wireless tag 40 saves data locally and later communicates data to wireless device 10 or external network 30 over a wired connection. Exemplary wired connections include a USB connection, although other suitable connections may also be used.

Figure 12:
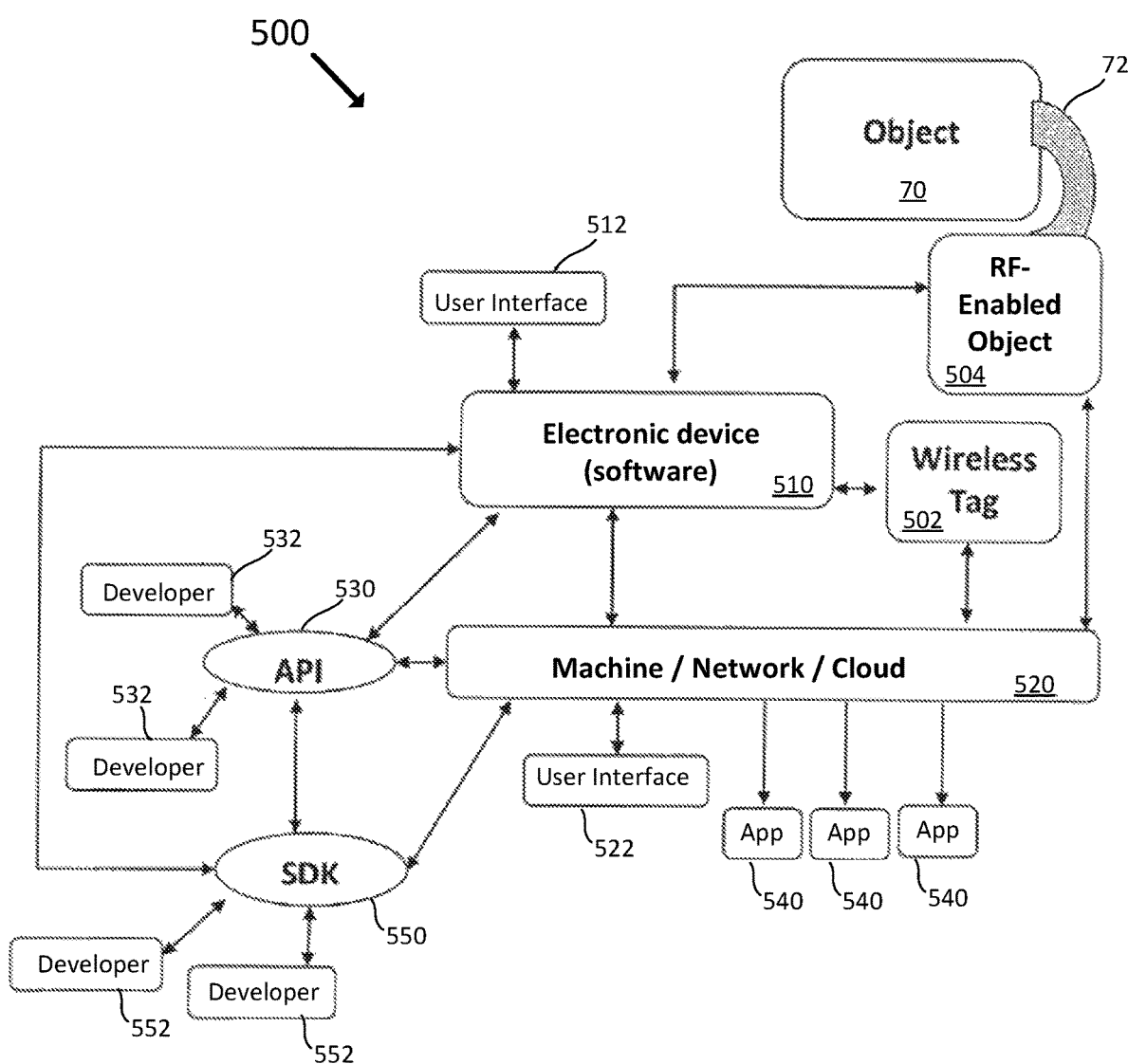
FIG. 12 illustrates an exemplary system architecture for providing an application programming interface and software development kit to developers for the disclosed system.

In one embodiment, at least one of the following communications channels is encrypted: between radio transceiver 56 and controller 48, between wireless tag 40 and electronic device 10, between radio transceiver 24 and controller 28, between electronic device 10 and external device 30, within components of external device 30, between external device 30 and an external user interface, such as user interface 522 (as illustrated in FIG. 12).

In one exemplary embodiment, data from data transmitter 18 and data receiver 20 is exchanged with data on external device 30. External device 30 may comprise a single device or a plurality of devices in communication with each other. In one embodiment, external device 30 is a machine capable of storing data, including, but not limited to a computer, a laptop computer, a tablet computer, a mobile electronic device, or a server. In another embodiment, external device 30 is a network capable of storing data, including but not limited to a local area network, a public switched network, a CAN network, and any type of wired or wireless network. In still another embodiment, external device 30 is a network or cloud data service. As used herein, a cloud service refers to remotely hosted data, remotely hosted servers, or both over the internet, web or a network which is accessible from multiple locations and devices or machines. As used herein, the term includes at least Infrastructure-as-a-Service (IaaS), Platform-as-a-Service (PaaS), Hardware-as-a-Service, and Software-as-a-Service (SaaS) service, and other remote data computation, application, management, or storage resources. As used herein, network, refers to a local area network, a private network, a public switched network such as but not limited to the Internet, a CAN network, and any type of wired or wireless network.

Figure 1B:
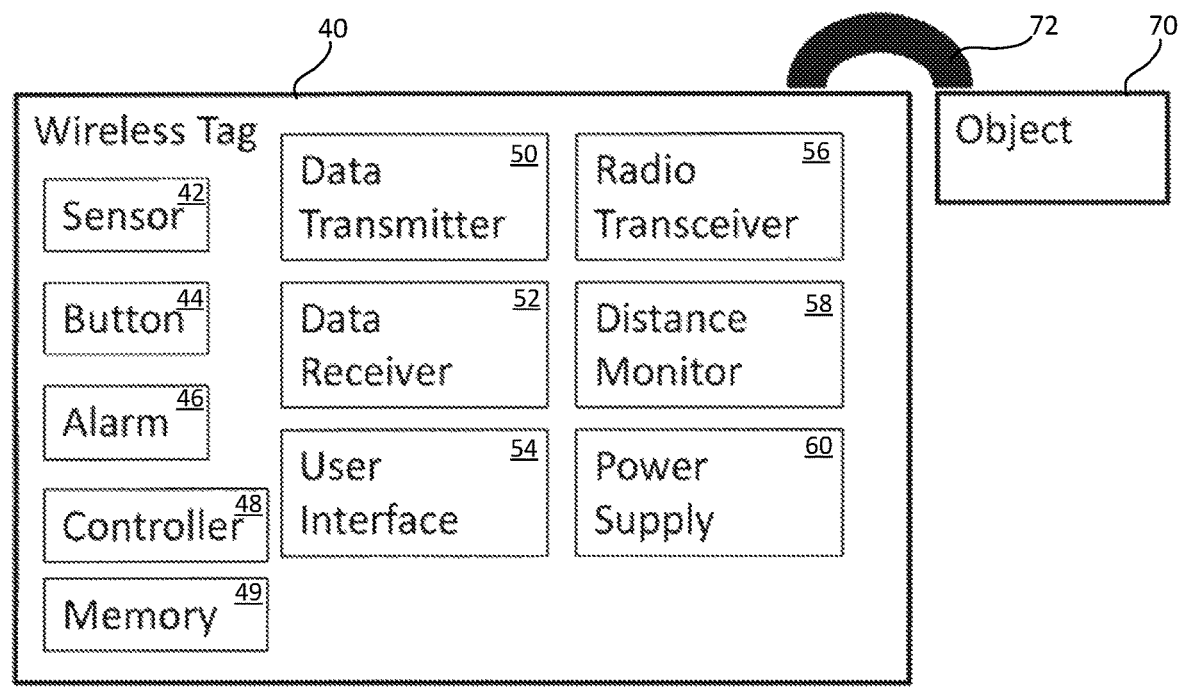
FIG. 1B illustrates an exemplary wireless tag for wireless communication with an electronic device or network.

Referring next to FIG. 1B, an exemplary wireless tag 40 is illustrated. In one embodiment, wireless tag 40 includes user interface 54 comprising one or more I/O modules which provide an interface between an operator and wireless tag 40. An operator may include a human operator or a computer, machine, or software application interfacing with wireless tag 40, electronic device 10, or external device 30. Exemplary I/O modules include input members and output members. Exemplary input members include buttons, such as button 44, switches, keys, a touch display, a keyboard, a sensor, a mouse, and other suitable devices for providing information to controller 48. Exemplary output devices include lights, a display (such as a touch screen), printer, speaker, visual devices, audio devices including alarm 46, tactile devices, and other suitable devices for presenting information to an operator.

In the exemplary embodiment illustrated in FIG. 1B, wireless tag 40 includes a plurality of hardware and software, including a controller 48. Controller 48 includes logic which may control operation of wireless tag 40. The logic of controller 48 may be implemented in hardware or in hardware executing software. Exemplary software may be stored in a memory 49. Memory 49 includes instructions executed by controller 48, as described for controller 28 above. Controller 48 may include one or more processors or other structures to implement the logic of controller 48.

In the exemplary embodiment illustrated in FIG. 1B, wireless tag 40 includes radio transceiver 56. Radio transceiver 56 sends and receives data from other radio transceivers, including radio transceiver 24 incorporated in electronic device 10. In one embodiment, radio transceiver 56 may comprise a single transceiver. In another embodiment, radio transceiver 56 comprises a separate transmitter and receiver.

In one embodiment, radio transceiver 56 is a Bluetooth (R) transceiver that operates on Bluetooth protocols. In another embodiment, radio transceiver 56 operates on RF protocols. In still another embodiment, radio transceiver 56 operates on NFC protocols. Other suitable radio transceivers may also be used. In one embodiment, at least some of the data exchanged is encrypted.

In the exemplary embodiment illustrated in FIG. 1B wireless tag 40 includes distance monitor 58. In one embodiment, distance monitor 58 monitors communication between radio transceiver 56 and electronic device 10. In another embodiment, distance monitor 58 may determine the status of the connection between electronic device 10 and wireless tag 40 to determine if the connection is dropped, broken, lost, or otherwise not present. In still another embodiment, distance monitor 58 may determine the distance or range between wireless tag 40 and electronic device 10.

In the exemplary embodiment illustrated in FIG. 1B, wireless tag 40 includes data transmitter 50 and data receiver 52. Data transmitter 50 and data receiver 52 function similarly to data transmitter 18 and data receiver 20 of electronic device 10. Data transmitter 50 sends data to external device 30, and data receiver 52 receives data from external device 30. In one exemplary embodiment, radio transceiver 56 also functions as data transmitter 50 and/or data receiver 52. In another exemplary embodiment, data transmitter 50 and data receiver 52 are separate from radio transceiver 56. In one embodiment, data transmitter 50 and data receiver 52 exchange data with external device 30 as described above. Other suitable mobile data standards may also be used. In one embodiment, at least some of the data exchanged is encrypted. In still another exemplary embodiment, wireless tag 40 does not include data transmitter 50 and/or data receiver 52.

In another embodiment, wireless tag includes power supply 60. Exemplary power supplies 60 include rechargeable batteries, including but not limited to nickel-cadmium and lithium ion batteries, and non-rechargeable batteries. Other suitable power supplies 60 may also be used.

In still another embodiment, wireless tag 40 includes one or more sensors 42. Exemplary sensors 42 include, but are not limited to, temperature sensors, altimeters, barometers, pressure sensors, humidity sensors, chronometers, pedometers, accelerometers, level sensors, impact sensors, and compasses. Other suitable sensors may be used depending on the desired application.

In yet still another embodiment, wireless tag 40 may include a GPS or other suitable location detection technologies (not shown). In this embodiment, wireless tag 40 may communicate its position over at least one of data transmitter 50 and radio transceiver 56. Using the communicated position information, a direction to wireless tag 40 may be displayed or communicated on user interface 22 or a user interface associated with external device 30. In one embodiment, the direction may be saved locally in memory 49 associated with the electronic device 10. In another embodiment, the direction may be communicated to the external device 30 and saved in memory 29 associated with the electronic device 10. In still another embodiment, the position may be saved locally in memory 29 associated with the wireless tag data and later communicated to wireless device 10 or external network 30 over a wired or wireless connection, such as network 31.

Figure 1C:
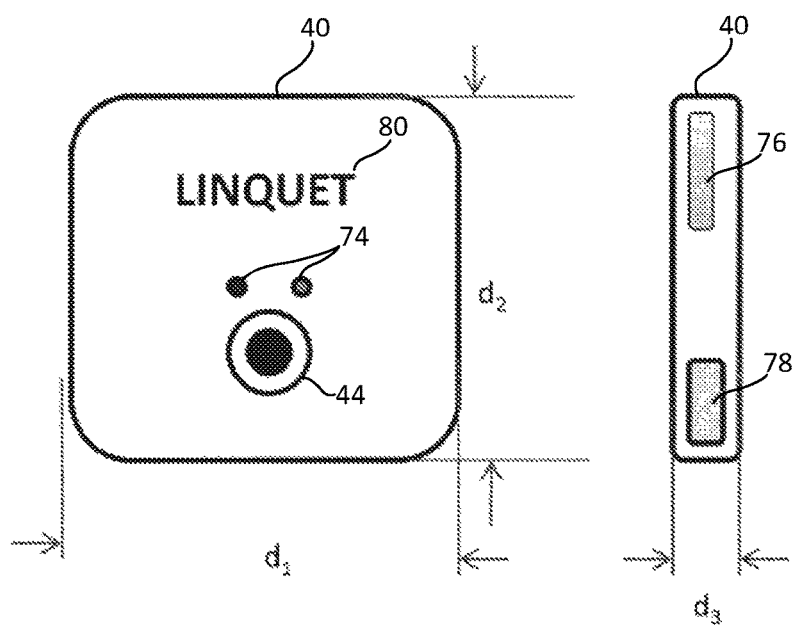
FIG. 1C illustrates an exemplary wireless tag for wireless communication with an electronic device or network.

Although shown separately the modules shown in FIG. 1 and FIG. 2 may include one or more other modules.

In yet another exemplary embodiment, wireless tag 40 includes securing element 72 to secure wireless tag to object 70. In one embodiment, object 70 is a person or animal. In another embodiment, object 70 is an inanimate physical object. In one embodiment, securing element 72 includes a mechanical or chemical fastener to secure wireless tag 40 to object 70. Other securing elements 72 may also be used. In another embodiment, wireless tag 40 is not secured to object 70, but is positioned near, in, or on object 70, or in an environment. Other positions of wireless tag 40 in relation to object 70 may also be used.

Referring next to FIG. 2B, an exemplary wireless tag 40 is illustrated. The exemplary wireless tag 40 includes a button 44, plurality of lights 74, and speaker 76 for alarm 46 as part of user interface 54. In other embodiments, other suitable inputs and outputs may be used. The exemplary wireless tag 40 also includes power socket 78 for recharging power supply 60. The exemplary wireless tag 40 also includes an area for displaying identifying information 80. In other embodiments, no information is displayed on wireless tag 40.

In the exemplary embodiment illustrated in FIG. 2B, wireless tag 40 has a first dimension d1, a second dimension d2, and a thickness d3. In one embodiment, first dimension and second dimension are about 0.5 cm to about 10 cm, although larger and smaller sizes may also be used. In another embodiment, first dimension and second dimension are about 4 cm to about 5 cm. In still other embodiments, other suitable dimensions depending on the intended use may be used.

In one exemplary embodiment, the thickness d3 of wireless tags 40 is relatively thin. In one embodiment, d3 is about 10 mm or less. In another embodiment, d3 is about 6 mm or less. In still another embodiment, d3 is more than about 10 mm. The thinner wireless tag 40 is, the less intrusively it can be attached to an object 70 for tracking. In yet still another embodiment, d3 is about 5 mm or less. The thinner wireless tag 40 is, the easier it can be stored in a wallet or purse. Thicker tags may be easier to manufacture and may require lower component prices.

Referring next to FIG. 3, exemplary data collected by one embodiment of the disclosed system is illustrated. FIG. 3A illustrates collecting exemplary data at two positions, point 1 and point 2. In one embodiment, points 1 and 2 are physically spaced apart. In another embodiment, points 1 and 2 are at the same absolute location, but are recorded at different points in time. FIG. 3B illustrates an exemplary table 110 storing the data collected in FIG. 3A. Exemplary data collected at point 1 include the time, the absolute position and direction determined by electronic device 10, the status of one or more wireless tags 40 as in range/out of range as determined by the electronic device 10, data from one or more sensors 42 attached to wireless tag 40, and the status of any command executed by controllers 28 and/or 48. Other suitable data may be collected and stored in table 110 as well. Similar data is collected at point 2. In one embodiment, the data in table 110 may be collected by wireless tag 40. In another embodiment, the data in table 110 may be collected by electronic device 10. In still another embodiment, the data in table 110 may be collected by a combination of wireless tag 40 and electronic device 10.

The exemplary data collected at points 1 and 2 in FIG. 3A is stored in the exemplary table illustrated in FIG. 3B. Table 110 may include more or fewer columns and rows than in the exemplary embodiment illustrated in FIG. 3. The different categories of data collected at each of point 1 and point 2 are organized in columns 112. The data from each point is organized in rows 114. In one embodiment, table 110 may be stored in memory a network, including in the cloud. In another embodiment, the data is stored locally in memory 29 on the electronic device 10 or memory 49 on the wireless tag 40. In one embodiment, the data is stored at multiple locations that can be queried to create table 110. In another embodiment, the data in table 110 is stored in memory on external device 30. In one embodiment, the data in table 110 is communicated to external device 30 by data transmitter 18 in electronic device 10 or across network 31. In another embodiment, the data in table 110 is communicated to external device 30 by data transmitter 50 in wireless tag 40. In still another embodiment, the data in table 110 is communicated to external device 30 by a combination of data transmitters 18, 50. In one embodiment, table 110 is accessible to a user through an internet browser or other software application. In another embodiment, table 110 data is presented directly to an operator, user, or machine. In still another embodiment, table 110 data is accessible through an application programming interface. In yet still another embodiment, table 110 data is accessible through a software development kit.

An exemplary method of using the disclosed system in an anti-loss or anti-theft embodiment is illustrated in FIGS. 4-5. FIG. 4 illustrates exemplary data collected by an anti-loss or anti-theft embodiment of the disclosed system. FIG. 4A illustrates collecting data at three positions. Points 1, 2, and 3 may be physically spaced apart, or one or more of points 1, 2, 3 may be at the same absolute location but recorded at different points in time. At points 1, 2, and 3, electronic device 10 sends data to external device 30 indicating the identification of electronic device 10 and wireless tag 40, the time, the speed, the absolute position of electronic device 10 as determined by absolute position module 14, and the status of wireless tag 40 as determined by distance monitor 26. FIG. 4 illustrates wireless tag 40 being out of range at point 3. The circles at positions 1 and 2 indicate that the distance between electronic device 10 and wireless tag 40 is less than the set allowable distance or range. The X at position 3 indicates that wireless tag 40 is located more than the set allowable distance or range from electronic device 10.

FIG. 4B illustrates a first exemplary table 140 storing the data collected in FIG. 4A. In table 140, electronic device 10, wireless tag 40, or both update data to external device 30 for every point 1, 2, 3. Therefore, table 140 includes a row for each of points 1, 2, and 3.

FIG. 4C illustrates second exemplary table 150 storing the data collected in FIG. 4A. In table 150, electronic device 10, wireless tag 40, or both update data to external device 30 only when the status indicates the distance or range between wireless tag 40 and electronic device 10 has exceeded the allowable distance or range. Using a table such table 140 allows for historical tracking of where the electronic device 10 had been, allowing a user to retrace her location record. Using a table such as table 150 requires less storage capacity. In one embodiment, the data in either table 140 or table 150 is also stored locally in memory 29 associated with electronic device 10 or memory 49 associated with wireless tag 40.

Figure 5A:
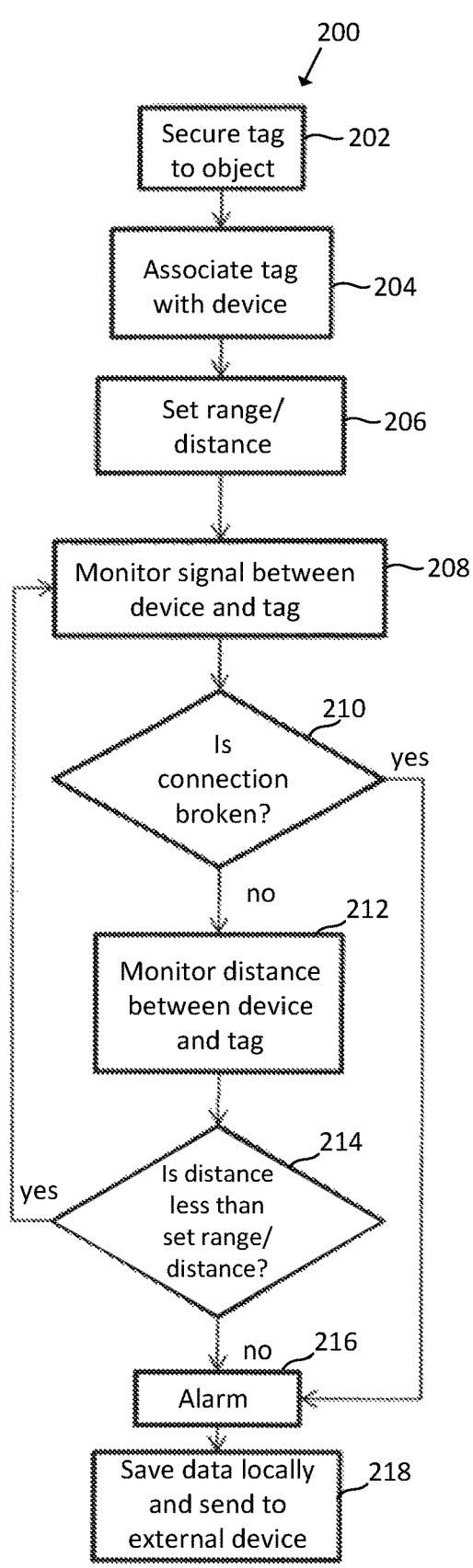
FIG. 5A illustrates exemplary processes of the disclosed system in an anti-loss or anti-theft embodiment.
Figure 5B:
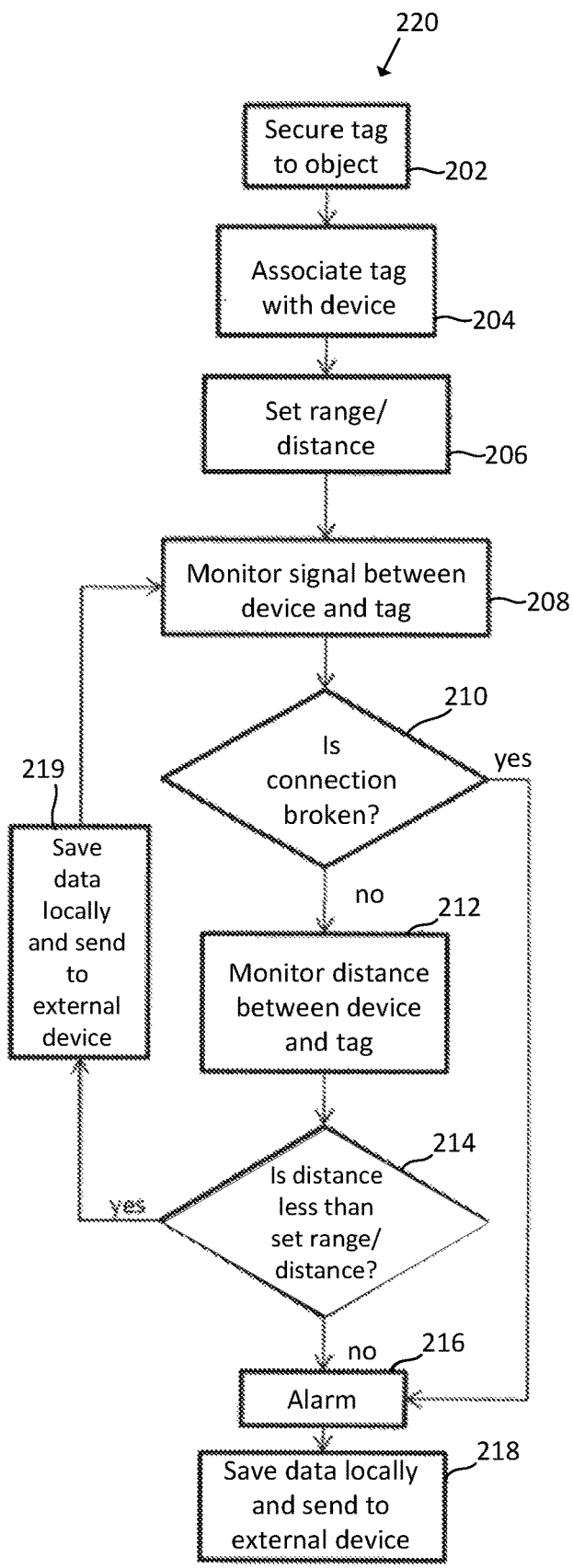
FIG. 5B illustrates exemplary processes of the disclosed system in an anti-loss or anti-theft embodiment.

FIGS. 5A and 5B illustrate exemplary processes 200, 220 of the disclosed system in an anti-theft or anti-loss embodiment. In FIG. 5A, the block 202 illustrates securing wireless tag 40 to object 70 that is to be tracked. Block 204 illustrates associating wireless tag 40 with electronic device 10. In one embodiment, block 204 includes selecting a name and/or icon for wireless tag 40. In another embodiment, associating wireless tag 40 is performed through user interface 22 on electronic device 10. In block 206, a range or distance between wireless tag 40 and electronic device 10 is selected. In one embodiment, the allowable distance or range is a default value. In another embodiment, the allowable distance is selected from a plurality of default values. In yet another embodiment, the distance is input by the user or machine. In still yet another embodiment, a user selects from a list of range choices, such as but not limited to Close, Mid, and Far, each of which is associated with a predetermined distance or signal strength. In block 208, the connection between wireless tag 40 and electronic device 10 is monitored by both controller 28 of electronic device 10 and controller 48 of wireless tag 40. If the connection between radio transceiver 24 and radio transceiver 56 is broken as shown in block 210, an alarm is activated in block 216 and data is saved locally to electronic device 10 and sent to external device 30 by data transmitter 18 of electronic device 10. In another embodiment (not shown) an additional predetermined action is taken or command is activated in addition to the alarm and data communication. In one embodiment, the alarm in block 216 is alarm/speaker 16 of electronic device 10. In another embodiment, the alarm in block 216 is alarm 46 of wireless tag 40. In still another embodiment, the alarm in block 216 is the both alarm/speaker 16 and alarm 46. In one embodiment, the data sent to external device 30 in block 218 includes at least one of position as determined by absolute position module 14, time, status as determined by distance monitor 26, and the last reading of sensor 42 received from wireless tag 40.

If in block 210 the connection is not broken, in block 212 the distance between electronic device 10 and wireless tag 40 as determined by distance monitor 26 is monitored. As shown in block 214, if the distance is less than the distance or range selected in block 206, the system returns to block 208 to monitor the connection. If the distance is not less than the set distance or range, an alarm is activated in block 216 and data is saved locally to electronic device 10 and sent to external device 30 as described above. In another embodiment (not shown) an additional predetermined action is taken or command is activated in addition to the alarm and data communication.

FIG. 5B illustrates a variant 220 of the exemplary anti-loss or anti-theft process described above. In the process illustrated in 5B, if the distance or range in block 214 is less than the distance selected in block 206, in block 219 data is saved locally to electronic device 10 and sent to external device 30 as in block 218 before returning to block 208 to monitor the connection. The process of FIG. 5B will generate a table similar to table 150 illustrated in FIG. 4C, while the process of FIG. 5A will generate a table similar to table 140 illustrated in FIG. 4B.

Figure 16C:
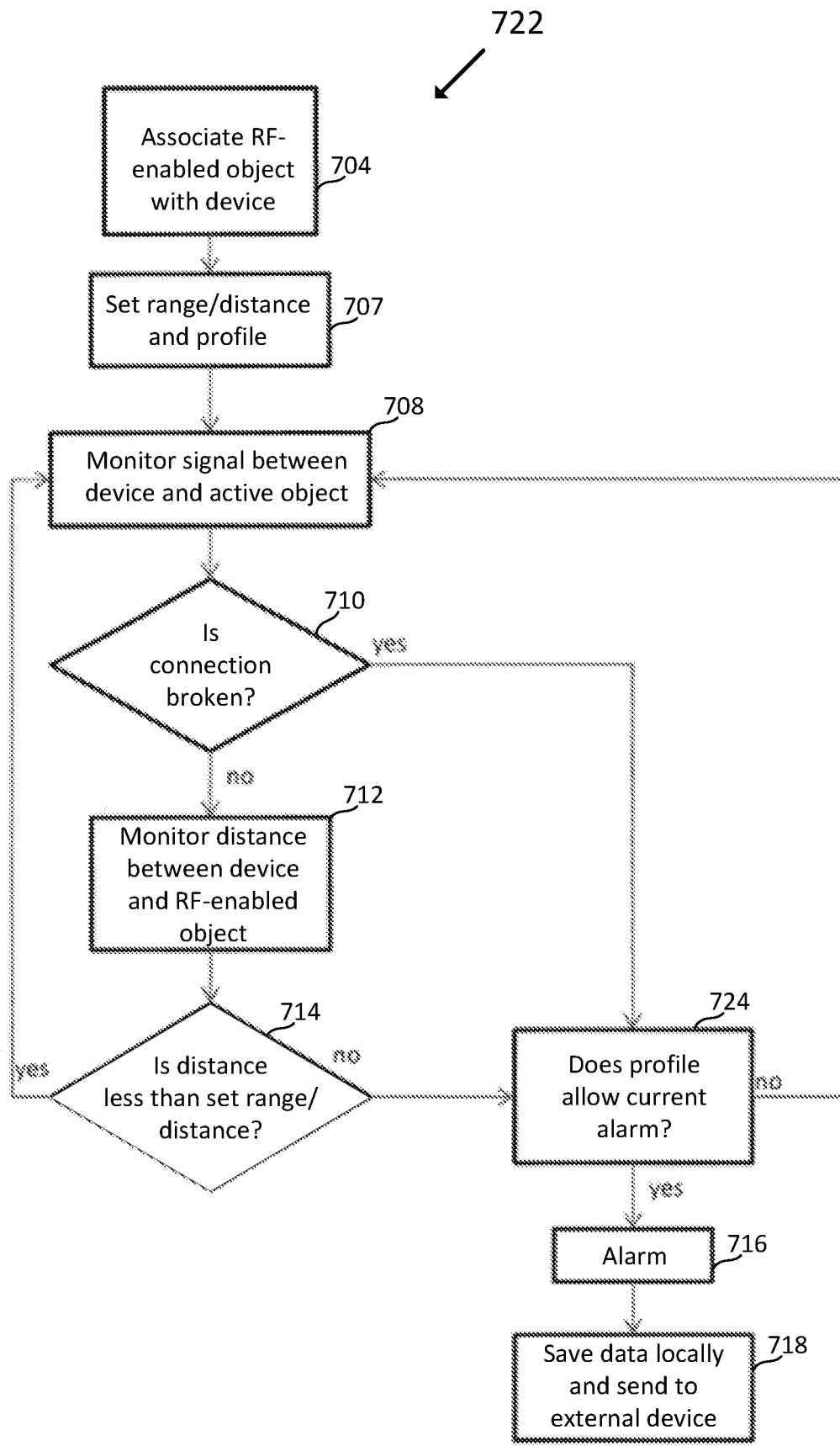
FIG. 16C illustrates exemplary processes of the disclosed RF-enabled object system in an anti-loss or anti-theft embodiment.
Figure 16D:
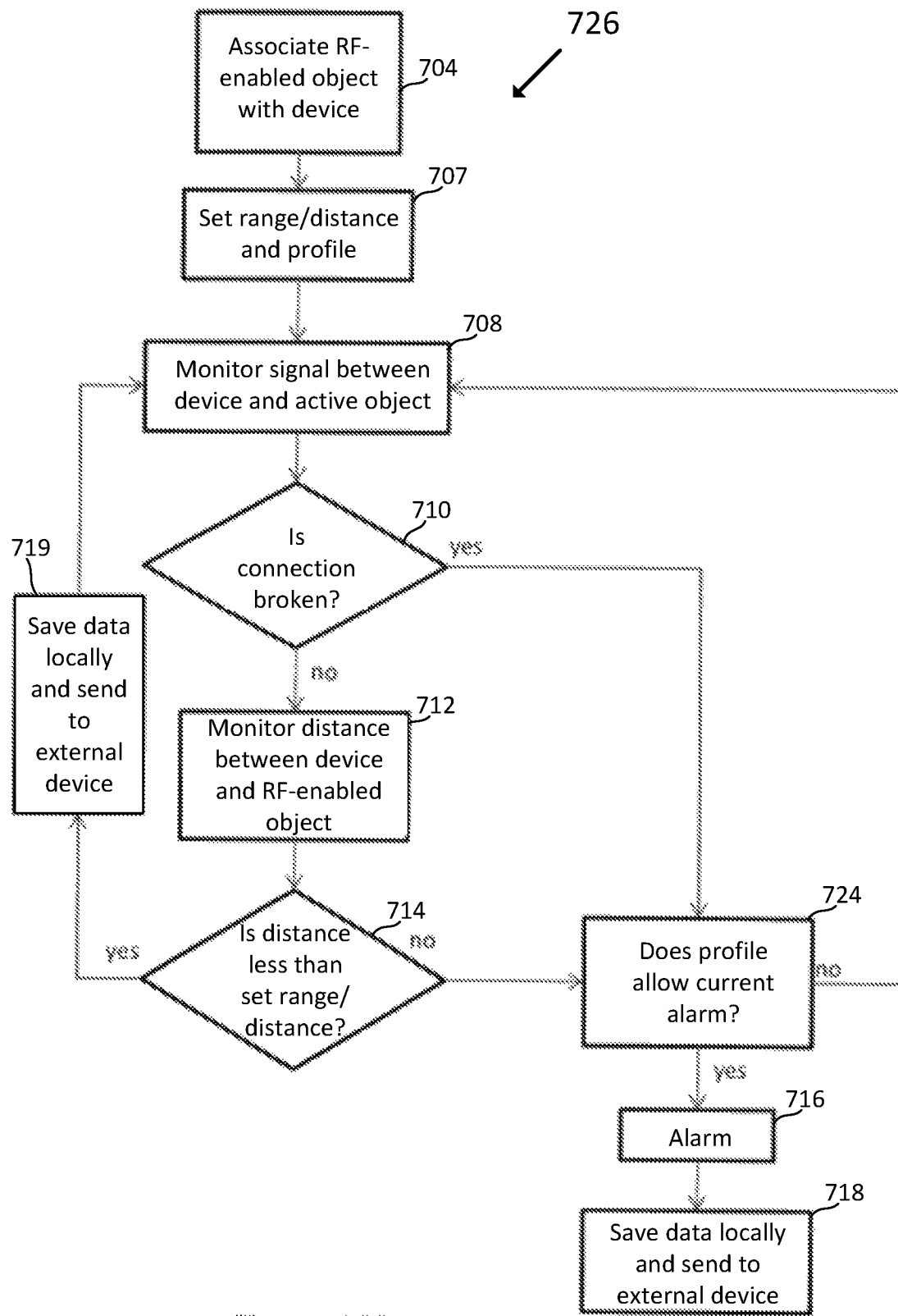
FIG. 16D illustrates exemplary processes of the disclosed RF-enabled object system in an anti-loss or anti-theft embodiment.

In some embodiments of processes 200, 220, in block 206 a profile is selected, similar to FIGS. 16C and 16D. In one embodiment, a profile is a set settings, where each setting is an action based on a predetermined condition. Exemplary settings include whether to alarm or not based on a predetermined condition, such as the location, the time, the temperature, etc. One exemplary setting is to disable the alarm during the weekends. Another exemplary setting is to disable the alarm in a predetermined location, such as a user's work. In these embodiments, if the connection is broken in block 210, or if the distance is less than the set range/distance in block 214, the system first determines whether the current profile settings allow for an alarm. If the profile allows for an alarm, the alarm is activated in block 216. If the profile does not allow for an alarm, the system returns to block 208 to monitor the signal.

Figure 6:
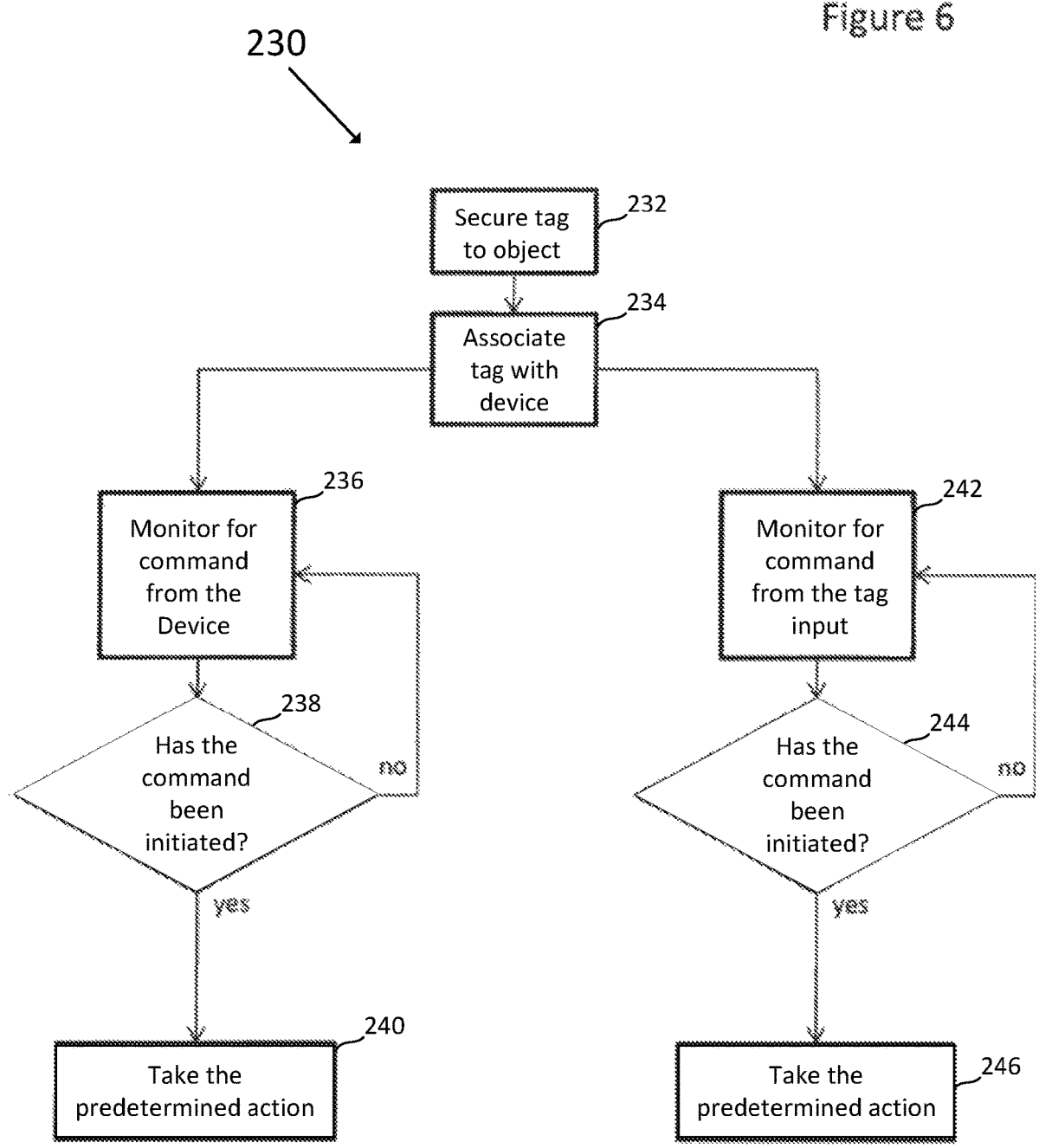
FIG. 6 illustrates an exemplary process of the disclosed system in a command embodiment.

FIG. 6 illustrates a general exemplary process 230 for responding to a predefined command from controller 28 of electronic device 10 or controller 48 or wireless tag 40. Block 232 illustrates securing wireless tag 40 to object 70 that is to be tracked. Block 234 illustrates associating wireless tag 40 with electronic device 10, as in block 204 of FIG. 5.

In block 236, controller 28 monitors the data from radio transceiver 56 for activation of a command. Exemplary commands include a panic alert, an exemplary illustration of which is given in FIG. 7 below, a finder command, and a position record command. Each command includes an associated predetermined action. The predetermined action may include more than one action. For example, a finder command from controller 28 may include the predetermined action of sounding alarm 46 for a short period to allow a user to find wireless tag 40. A similar command from controller 48 may allow a user to find electronic device 10. A reading command from controller 28 may include the predetermined action of sending data from sensor 42 to transceiver 56 or transmitter 50 for recording on electronic device 10 and/or machine/network/cloud. A position record command from controller 28 may include the predetermined action of sending the position as determined by module 14 for recording on electronic device 10 and/or on external device 30. Other suitable commands and predetermined actions may also be used. In block 238, if no command has been initiated, the system returns to block 236 to monitor for a command. If a command has been initiated, in block 240 the predetermined action is taken.

Similarly, in block 242, controller 48 monitors the data from radio transceiver 24 for activation of a command. Exemplary commands include the commands given for controller 28 above. Each command includes an associated predetermined action, as described for controller 28 above. In block 244, if no command has been initiated, the system returns to block 236 to monitor for a command. If a command has been initiated, in block 246 the predetermined action is taken.

In another embodiment, controller 48 may activate a command such as in FIG. 6 due to a reading of sensor 42 or the result of comparing the reading of sensor 42 to a predetermined value.

FIGS. 7A and 7B illustrate exemplary processes 250, 270 of the disclosed system in a panic-mode embodiment. In process 250, block 252 illustrates securing wireless tag 40 to object 70 that is to be tracked. Block 254 illustrates associating wireless tag 40 with electronic device 10, as in block 204 of FIG. 5. In block 256, controller 28, monitors the data from radio transceiver 24 for activation of Panic Alert Mode. In block 258, if no command has been initiated, the system returns to block 256 to monitor for a command. If a command has been initiated, in block 260, at least one of alarms 16, 46 is activated, data including position as determined by module 14 is stored locally and sent to external device 30, and in block 264 an alert is sent to at least one predetermined contact. In another embodiment (not shown) an additional predetermined action is taken or command is activated in addition to the alarm and data communication. The predetermined contact may be an emergency contact number, a law enforcement number, or a personal contact. In another embodiment, the contact may be a phone number or email address or other contact information. The alert may include time of mode activation, position as determined by module 14, time, and/or status as determined by distance monitor 26, and/or the reading of sensor 42.

FIG. 7B illustrates a variant 270 of the exemplary panic alert process described above. In the process illustrated in 7B, the predetermined action includes in block 266 selecting a contact list based in part on the current location as determined by module 14 or the time, and in block 268 sending an alert as in block 264, but to the contact list selected in block 266. In one embodiment, the selection in block 266 is based on a pre-selected set of criteria defined by the user. In another embodiment, the selection in block 266 is a default set of criteria. In still another embodiment, the selection in block 266 is from a default set of contacts, such as emergency contact numbers, and the selection is based at least in part on the current location as determined by module 14. In another embodiment, the selection is based at least in part on the current time.

FIGS. 8A and 8B illustrates exemplary processes 280, 310 of the disclosed system in a marketing embodiment. FIG. 8A illustrates an exemplary process 280 for giving a promotion based on finding a plurality of objects 70 each attached to a wireless tag 40. In block 282, a plurality of wireless tags 40 are attached to a plurality of objects 70 or placed in a plurality of different locations. In one exemplary embodiment, the tags are then spaced apart from each other. In another exemplary embodiment, the tags are spaced around a building or geographical area. In block 284, each wireless tag 40 is associated with a first device and a set distance or range for each wireless tag 40 is selected. In one exemplary embodiment, first device is electronic device 10. In another exemplary embodiment, first device is a machine/network/cloud in communication with data transmitters 50 and data receivers 52 or wireless tags 40.

In block 286, a user with a second device approaches one of wireless tags 40. In one exemplary embodiment, second device is an electronic device 10. In another exemplary embodiment, user must search the area to find objects 70 attached to wireless tags 40. As the second device approaches a wireless tag 40, in block 288, the distance between wireless tag 40 and second device is monitored by distance monitor 26 on second device and/or distance monitor 58 on wireless tag 40. In block 290, if the distance determined by distance monitor 26 or distance monitor 58 is more than the set distance or range given in step 284, the system returns to step 288 to monitor the distance. If the distance is less than the set distance or range, then in step 292, data regarding the "find" is saved locally on the first device and sent to external device 30. In step 294, an alert is displayed on second device, alerting the user that she has "found" the tag 40, and a status relating to that tag 40 on external device 30 is updated. In one embodiment, blocks 286 through 294 are repeated for multiple wireless tags 40. In another embodiment, multiple users with multiple electronic devices 10 each perform blocks 286 through 294.

In step 296, the system determines whether all tags 40 have been found. In one exemplary embodiment, the determination is made based on whether the tags 40 have been found by any user. In another exemplary embodiment, the determination is made based on whether the second device has found all of the tags 40. In still another exemplary embodiment, the determination is made based on a predetermined number of tags 40 that must be found. In yet still another exemplary embodiment, the tags 40 may be found by one or more users. If all tags 40 have not been found, then the system returns to block 286 and the user holding the second device approaches a second tag 40. If the system determines in block 296 that all tags 40 have been found, then a promotion is displayed on a user interface of second device, such as user interface 22 of electronic device 10. In one exemplary embodiment, the promotion is a discount or coupon, or a reward or point credit in a rewards or point system. In another exemplary embodiment, the promotion is an advertisement. In still another exemplary embodiment, the promotion depends upon how many tags 40 were found by the user or how quickly tags 40 were found by the user. In yet still another exemplary embodiment, the promotion is an alert that all tags 40 have been found. Other suitable promotions may also be used.

FIG. 8B illustrates an exemplary process 310 for providing a promotional game based on finding a plurality of categories of objects 70, each object attached to a wireless tag 40. In block 312, a plurality of wireless tags 40 are attached to a plurality of objects 70 or placed in a plurality of different locations. In one exemplary embodiment, the tags 40 are then spaced apart from each other. In another exemplary embodiment, the tags 40 are spaced around a building or geographical area. In block 314, each wireless tag 40 is categorized into one or more categories based on the object 70 attached to it or location it is placed in, and a distance or range is set for each category. In another embodiment, a time is set for each category, and the tags 40 associated with the category must be found within that time or the electronic device 10 must be within the distance or range for that amount of time. In block 316, a list of categories is provided to a device. In one exemplary embodiment, device is an electronic device 10.

In block 318, a user with device approaches one of wireless tags 40. In another exemplary embodiment, user must search the area to find objects 70 attached to wireless tags 40. As the device approaches a wireless tag 40, in block 320, the distance between wireless tag 40 and device is monitored by distance monitor 26 on device and/or distance monitor 58 on wireless tag 40. In block 324, if the distance determined by distance monitor 26 or distance monitor 58 is more than the distance or range set in step 314, the system returns to step 320 to monitor the distance. If the distance is less than the set distance or range, then in step 326 the system determines whether the object category status is "found" for device. In one exemplary embodiment, this determination is performed by controller 28 on electronic device 10. If the category is already "found," then the system returns to block 318 to find another tag 40. If the category is not "found," in block 328, data regarding the "find" is saved locally on the device and sent to external device 30. An alert is displayed on second device, alerting the user that she has "found" the category, and a status relating to that tag 40 on external device 30 is updated. In another embodiment, rewards or points are earned by a user or group of users based on predetermined game or event rules or regulations.

In step 332, the system determines whether all categories defined in block 316 have been found. In one exemplary embodiment, the determination is made based on whether the categories have been found by any user. In another exemplary embodiment, the determination is made based on whether the device has found all the categories. In still another exemplary embodiment, the determination is made based on a predetermined number of categories that must be found. If all categories have not been found, then the system returns to block 318 and the user holding the device approaches a second tag 40. If the system determines in block 332 that all categories have been found, then in block 334 an alert is displayed on a user interface of device, such as user interface 22 of electronic device 10. In one exemplary embodiment, the alert is a promotion such as a discount or coupon. In another exemplary embodiment, the alert is an advertisement. In still another exemplary embodiment, the alert depends upon how many categories were found by the user or how quickly categories were found by the user or by point values associated with each category found by the user. In yet still another exemplary embodiment, the alert gives the user a reward or points in a predetermined system. Other suitable alerts may also be used.

Figure 9A:
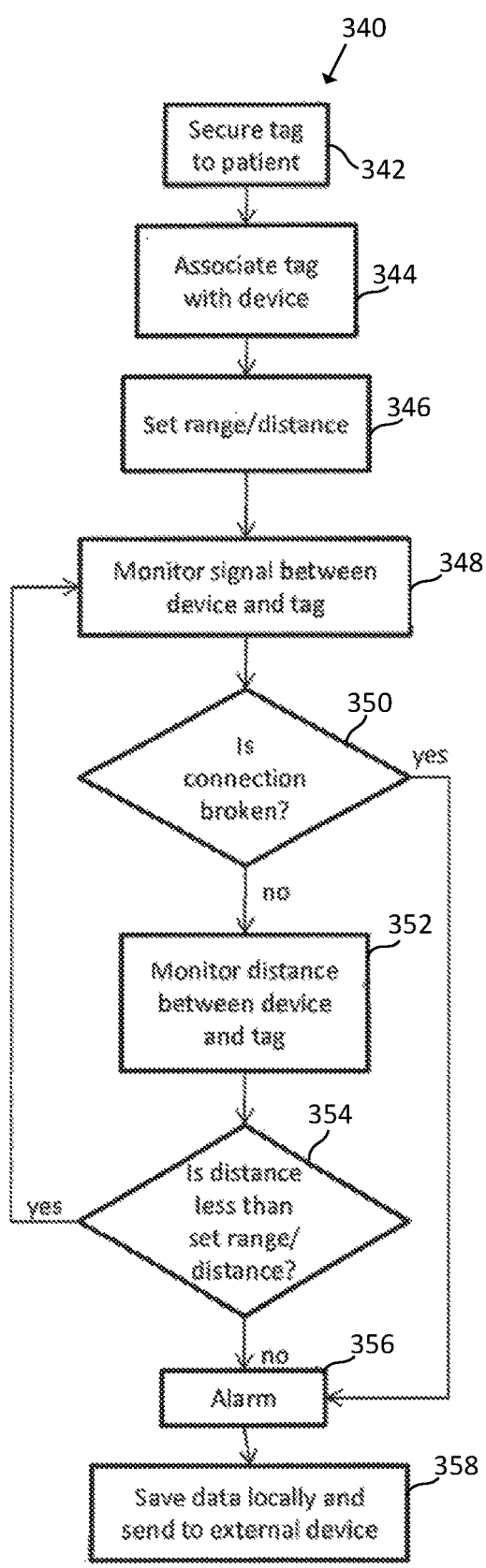
FIG. 9A illustrates exemplary processes of the disclosed system in a health-care embodiment.
Figure 9B:
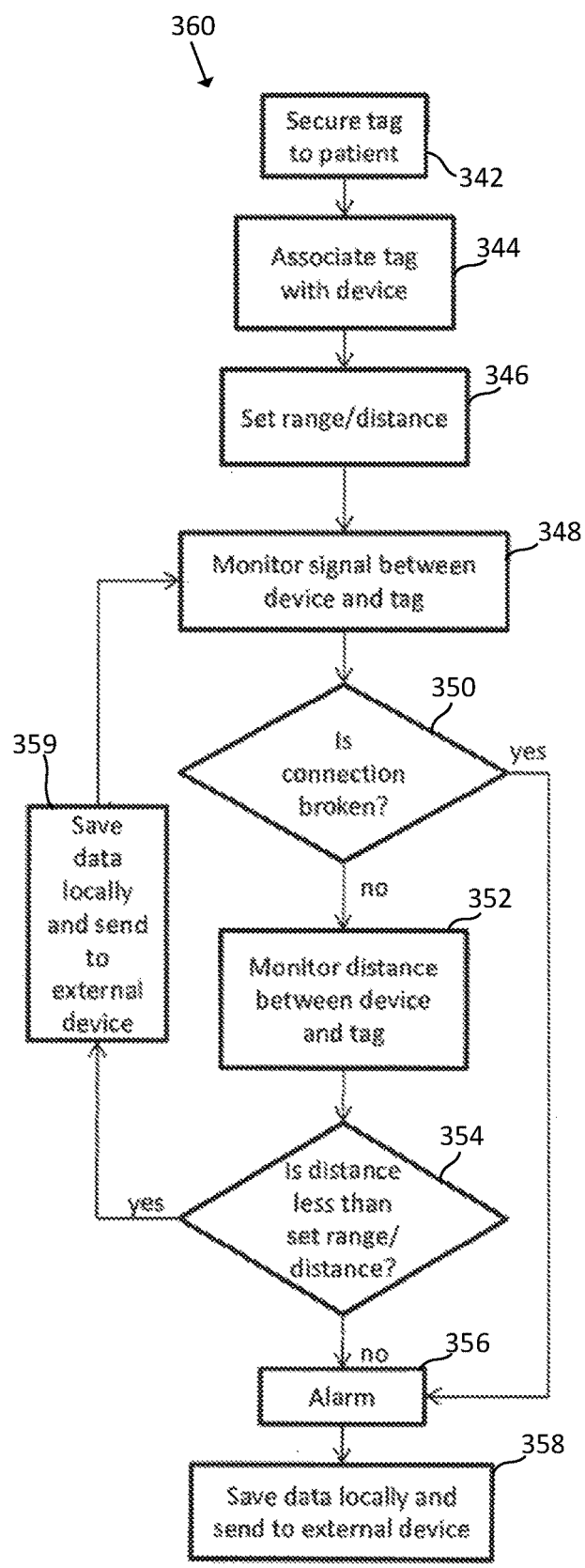
FIG. 9B illustrates exemplary processes of the disclosed system in a health-care embodiment.

FIGS. 9A and 9B illustrate exemplary processes 340, 360 of the disclosed system in a health-care patient monitoring embodiment. In FIG. 9A, block 342 illustrates securing wireless tag 40 to a patient that is to be tracked. Block 204 illustrates associating wireless tag 40 with electronic device 10. In one embodiment, block 344 includes selecting a name and/or icon for wireless tag 40. In another embodiment, associating wireless tag 40 is performed through user interface 22 on electronic device 10. In block 346, a distance or range between wireless tag 40 and electronic device 10 is selected. In one embodiment, the set distance or range is a default value. In another embodiment, the distance or range or time is selected from a plurality of default values. In yet another embodiment, the distance or range is input by the user. In block 348, the connection between wireless tag 40 and electronic device 10 is monitored by both controller 28 of electronic device 10 and controller 48 of wireless tag 40. If the connection between radio transceiver 24 and radio transceiver 56 is broken as shown in block 350, an alarm is activated in block 216 and data is saved locally to electronic device 10 and sent to external device 30 by data transmitter 18 of electronic device 10. In one embodiment, the alarm in block 356 is alarm/speaker 16 of electronic device 10. In another embodiment, the alarm in block 356 is alarm 46 of wireless tag 40. In still another embodiment, the alarm in block 356 is the both alarm/speaker 16 and alarm 46. In one embodiment, the data sent to external device 30 in block 358 includes at least one of position as determined by absolute position module 14, time, status as determined by distance monitor 26, and the last reading of sensor 42 received from wireless tag 40.

If in block 350 the connection is not broken, in block 352 the distance between electronic device 10 and wireless tag 40 as determined by distance monitor 26 is monitored. As shown in block 354, if the distance or range is less than the distance or range selected in block 346, the system returns to block 348 to monitor the connection. If the distance or range is more than the set distance or range, an alarm is activated in block 356 and data is saved locally to electronic device 10 and sent to external device 30 as described above.

FIG. 9B illustrates a variant 360 of the exemplary health care patient monitoring embodiment described above. In the process illustrated in FIG. 9B, if the distance in block 354 is less than the distance selected in block 346, in block 359 data is saved locally to electronic device 10 and sent to external device 30 as in block 358 before returning to block 348 to monitor the connection.

Figure 10:
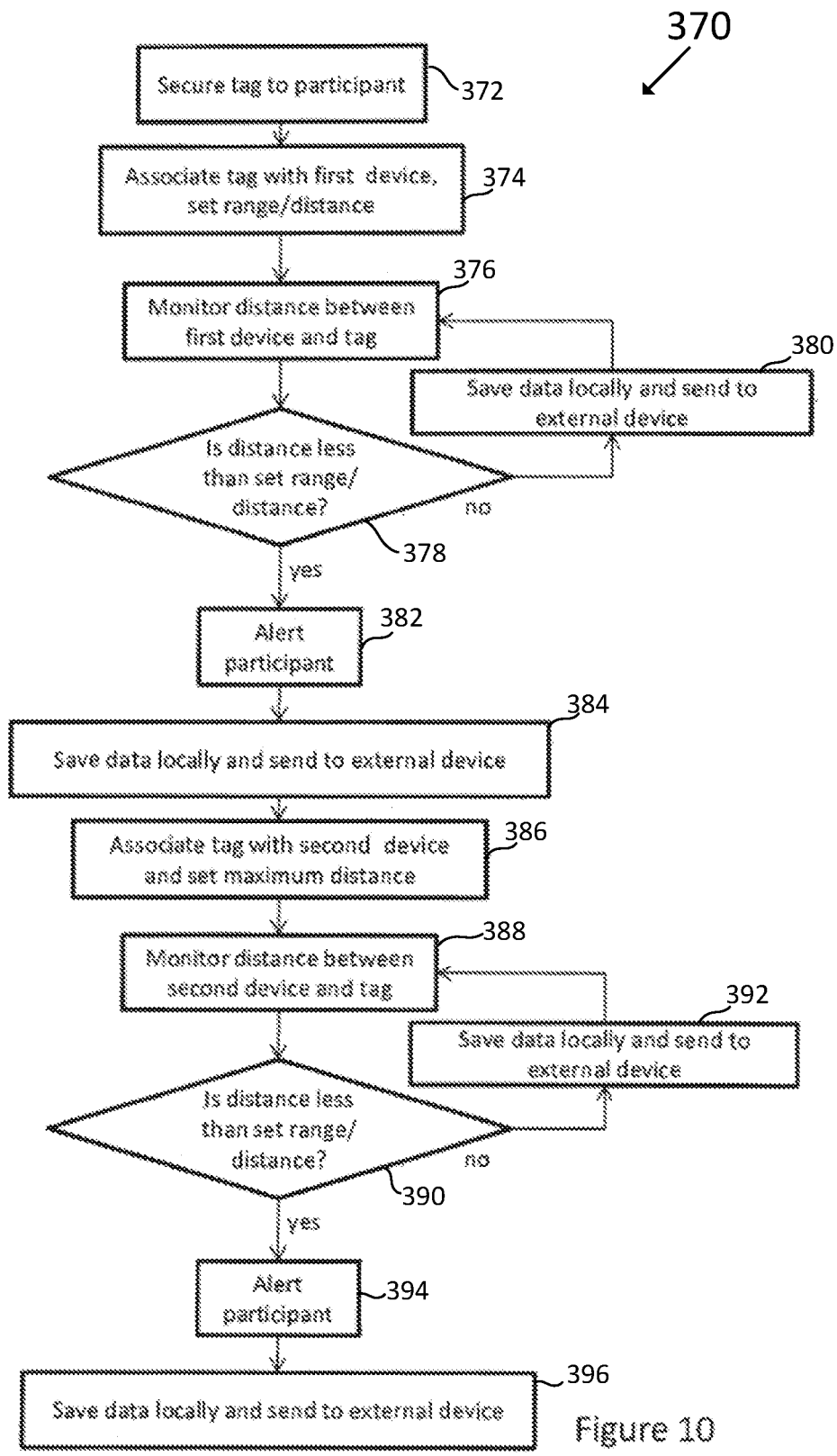
FIG. 10 illustrates an exemplary process of the disclosed system in an athletic competition embodiment.

An exemplary method of using the disclosed system in an athletic competition embodiment is illustrated in FIGS. 10-11. FIG. 10 illustrates exemplary athletic competition processes 370 of the disclosed system. In block 372, wireless tag 40 is secured to an athletic participant who is to be tracked. Exemplary athletic participants include, but are not limited to, runners, skiers, motorsport drivers, and other suitable participants. Wireless tag 40 may be secured to the participant or a group of participants, to the participant's gear or equipment, or in another suitable location. Block 374 illustrates associating wireless tag 40 with a first electronic device 10 and setting a distance or range. In one embodiment, block 374 includes selecting a name and/or icon for wireless tag 40. In another embodiment, associating wireless tag 40 is performed through user interface 22 on electronic device 10. In one embodiment, the set distance or range is a default value. In another embodiment, the distance or range is selected from a plurality of default values. In yet another embodiment, the allowable distance or range is input by the user. In block 376, the distance between electronic device 10 and wireless tag 40 as determined by distance monitor 26 is monitored. As shown in block 378 if the distance or range is less than the distance or range selected in block 206, the system returns to block 376 to monitor the connection. In one embodiment, data is uploaded to external device 30 in block 380. Exemplary data may include any combination of time, position, speed, sensor readings, and status. If the distance is less than the set distance or range, in block 382, the participant is alerted by wireless tag 40. In one exemplary embodiment, the alert is through alarm 46. In another exemplary embodiment, the alert is through user interface 54. Other suitable alerts may also be used. In block 384, data is uploaded to external device 30 as in block 380.

Block 386 illustrates associating wireless tag 40 with a second electronic device 10 and setting a second distance or range, similar to block 374. In one embodiment, all associating steps are performed together. In another embodiment, the same set distance or range is used for all associating steps. In block 388, the distance between electronic device 10 and wireless tag 40 as determined by distance monitor 26 is monitored. As shown in block 390 if the distance is less than the distance selected in block 206, the system returns to block 376 to monitor the connection. In one embodiment, data is uploaded to external device 30 in block 392. If the distance is less than the set distance or range, in block 394, the participant is alerted by wireless tag 40. In one exemplary embodiment, the alert is through alarm 46. In another exemplary embodiment, the alert is through user interface 54. Other suitable alerts may also be used. In block 396, data is uploaded to external device 30 as in block 392.

Figures 11A, 11B:
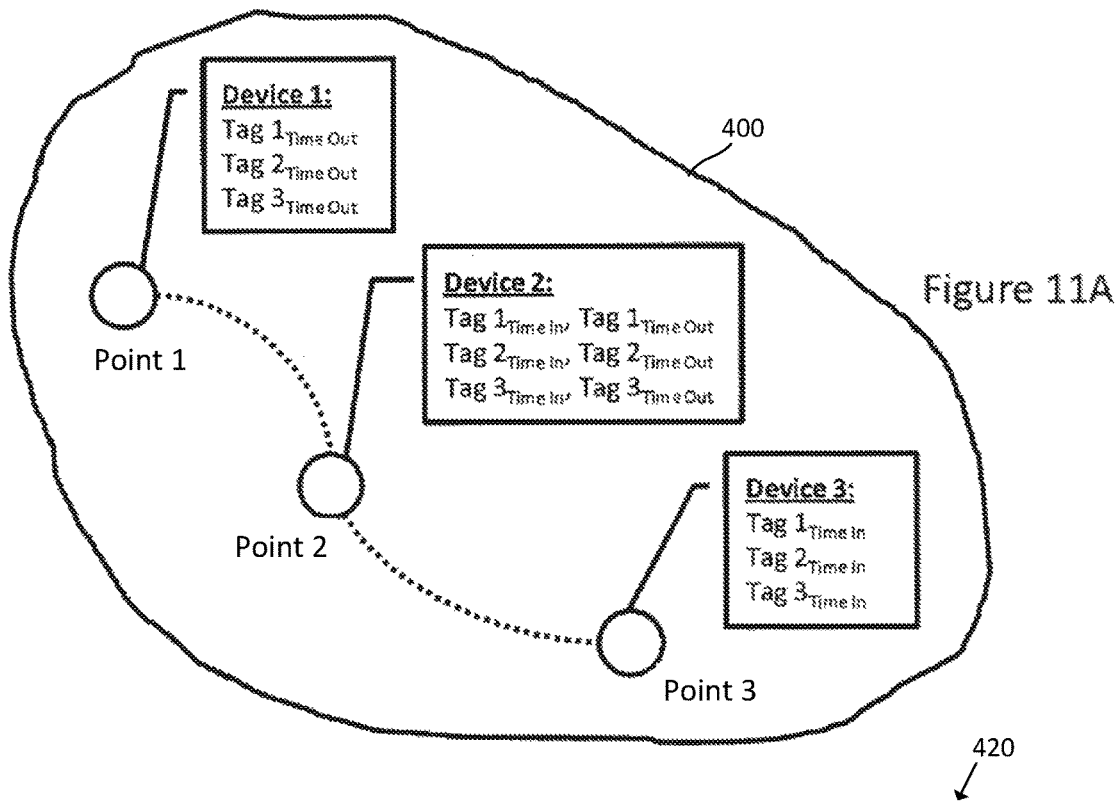
FIG. 11A illustrates exemplary data collected by an athletic competition embodiment of the disclosed system collecting data at three positions.
FIG. 11B illustrates an exemplary table storing the data collected in FIG. 11A.

FIG. 11 illustrates exemplary data collected by an athletic competition embodiment of the disclosed system. FIG. 11A illustrates collecting data at three positions, points 1, 2, and 3, which may be physically spaced apart from each other. In FIG. 11A, a race starts at point 1, passes through point 2, and ends at point 3. At each of points 1, 2, and 3, a stationary electronic device 10 sends data to external device 30 indicating the identification of electronic device 10 and wireless tag 40, the absolute position of electronic device 10 as determined by absolute position module 14, and the status of wireless tag 40 as determined by distance monitor 26. FIG. 11B illustrates exemplary table 420 for storing the data collected in FIG. 11A. In one embodiment, the table 420 is also stored locally in memory 29 associated with electronic device 10 or in memory 49 associated with wireless tag 40. In table 420, electronic device 10, wireless tag 40, or both update data to external device 30 for each point 1, 2, 3. Table 420 stores data showing when wireless tag 40 and attached participant entered and left a range defined by the set distance or range around the electronic device 10 at each of points 1, 2, and 3.

In an alternative athletic competition embodiment, not shown, the athletic participants are provided with electronic device 10 and a wireless tag 40 is positioned at each of points 1, 2, and 3. In this embodiment, the data communicated to external device 30 for each point 1, 2, 3, may include the speed of the device 10 at each point. In another embodiment, each tag 40 periodically collects data from electronic devices 10 in range and uploads data to the external device 30. The data may include, but are not limited to, status of electronic devices 10 as in range or out of range, distance to the tag 40, signal strength, absolute position of the electronic device 10 (which may include latitude, longitude, and altitude), time, and speed of the electronic device 10. Other suitable arrangements may also be used.

FIG. 12 illustrates providing an API to developers for the disclosed system to allow developers the ability to create their own software and applications on top of the system. Providing an API allows developers to create customized and creative applications based on the system architecture 500. Also, it allows developers to distribute and monetize their software and applications or, indirectly, their other products and services. Within the exemplary system architecture 500 illustrated in FIG. 12, a first wireless tag 502 and a second wireless tag 504 are provided. In one embodiment, first wireless tag 502 and second wireless tag 504 are both wireless tags 40 as previously described. Wireless tag 502 is not attached to an object 70. Wireless tag 504 is attached to object 70 with securing element 72. Additional wireless tags may also be provided. Wireless tags 502, 504 are in communication with electronic device 510. In one embodiment, electronic device 510 is an electronic device 10 as previously described. Electronic device 510 includes a software program or application for communicating with wireless tags 502, 504 and/or a machine/network/cloud 520. In one embodiment, machine/network/cloud 520 is an external device 30. The software program or application includes a user interface 512. In one embodiment, user interface 512 is user interface 22. Machine/network/cloud also includes a user interface 522. In one embodiment, user interfaces 512, 522 provide access to data, programs, and applications stored locally on electronic device 510 and machine/network/cloud 520.

In one embodiment, user interface 522 allows a user to view, query, organize, and categorize data stored on external device 30, 520 gathered through data sent by electronic devices 510 and wireless tags 502, 504. In another embodiment, user interface 522 can be used to initiate commands or activate alarms on wireless tags 502, 504, and electronic device 510. In still another embodiment, user interface 522 allows a user to lock, remotely backup or wipe reset electronic device 510 having a software program or application for communicating with wireless tags 502, 504.

In one exemplary embodiment, system architecture 500 includes an API 530. API 530 is in communication with machine/network/cloud 520 and electronic device 510. In one embodiment, API 530 provides access to one or more of developers 532 to data stored on machine/network/cloud 520 and/or electronic device 510. Using this access, developers 532 can create a plurality of applications 540. In another embodiment, developers 532 use API to integrate applications 540 as part of system 500 in presentation to users through user interfaces 512, 522.

In another exemplary embodiment, system architecture 500 includes a software development kit (SDK) 550. In one embodiment, SDK 550 includes tools that may be used by software developers in developing software applications 540. In another embodiment, SDK 550 is in communication with machine/network/cloud 520 and electronic device 510. As illustrated, SDK 550 may also be in communication with API 530. In one embodiment, SDK 550 provides access to a plurality of developers 552 to data stored on machine/network/cloud 520, electronic device 510, and/or API 530. Using this access, developers can create a plurality of applications 540.

Applications 540 may be downloaded by users to their electronic device such as that shown in 510, to a machine/network/cloud such as that shown in 520, or reside on a machine/network/cloud and accessed through a web browser or other suitable software and/or user interface from an electronic device, such as 510, or a server. In one exemplary embodiment, the electronic device could be connected to or integrated into another suitable object or device such as, but not limited to, clothing, sporting goods, food, medicine, medical devices, furniture, livestock, animals, cars, packaging, or luggage.

In still another exemplary embodiment, developers 532 can use system architecture 500 to distribute and monetize their applications 540 to users. A variety of monetization strategies are considered, including providing applications for free to increase awareness, providing a series of paid advertisements with a free application, providing a free basic version and a fee premium version of an application, providing only a fee version of an application, and providing a free version but provide opportunities to purchase additional features, subscriptions, goods, or services within the application. Other suitable strategies may also be used.

In one exemplary embodiment, a method of distributing wireless tags 502, 504 is disclosed. In one embodiment, wireless tags 502, 504 are provided free of charge to clients for use with a free software program or application for an electronic device 510. The hardware of wireless tags 502, 504 and data communications of wireless tags 502, 504 may be encrypted. The wireless tags 502, 504 and electronic device 510 provide data to a machine/network/cloud 520 as described above. Clients are granted limited access to the data for a fee. In one exemplary embodiment, a fee, such as a periodic or monthly fee, is charged for access to data regarding a wireless tag 502 or 504. Other exemplary fees include one-time, subscription, and pay-as-you-go fees. In another exemplary embodiment, a periodic fee for each wireless tag 502, 504 allows the client access to the API 530 for creating applications 540 for data from the paid wireless tags 502, 504. In still another exemplary embodiment, applications 540 through API 530 allow commands to be executed from user interface 512 or user interface 522 accessible to the client through an internet webpage or a similar medium. In yet still another exemplary embodiment, different tiers of access to machine/network/cloud 520 and software on electronic device 510 are provided to different clients, where each tier has an associated periodic fee. Combination of all of the strategies disclosed may also be used.

Figures 13, 13B:
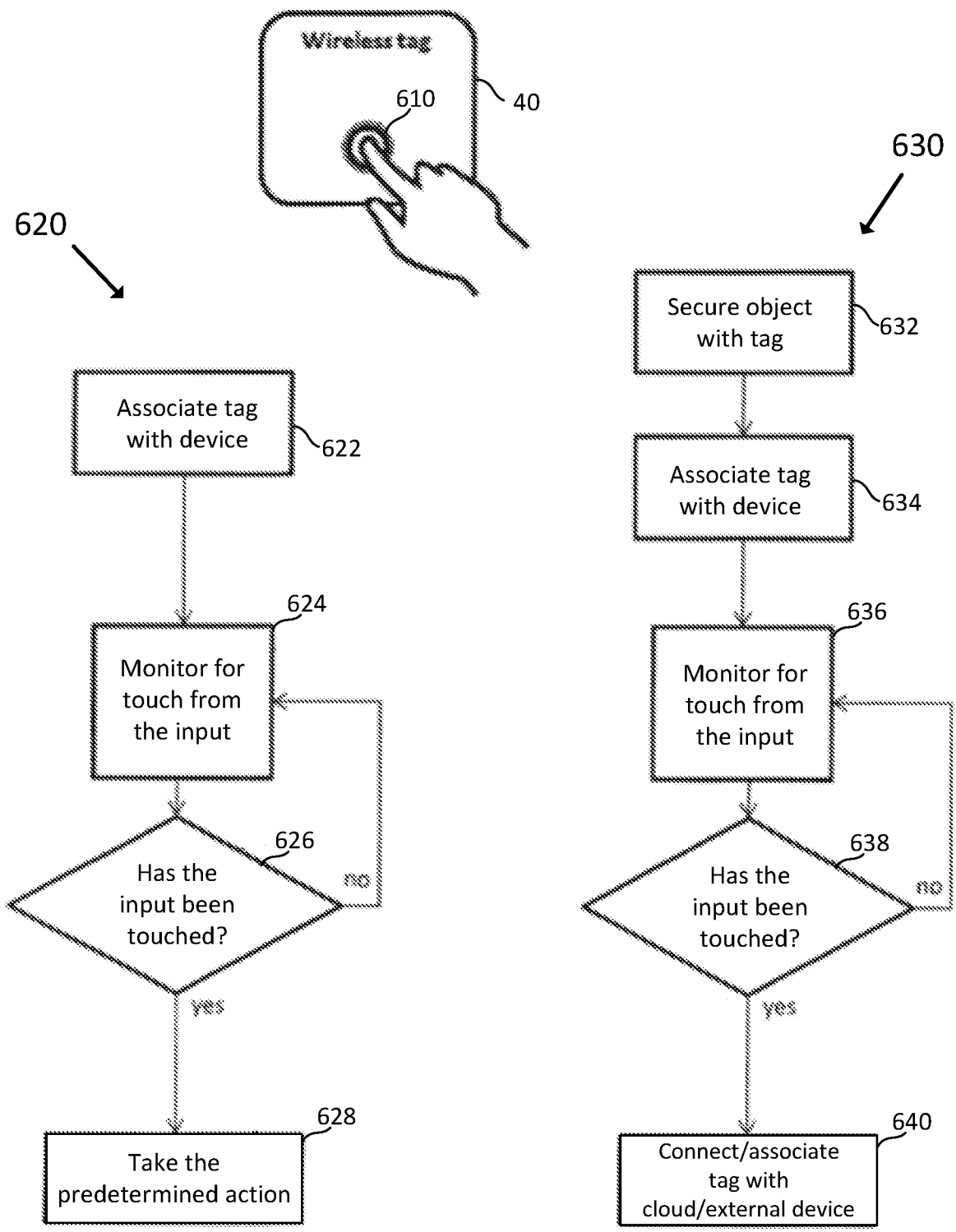
FIG. 13 illustrates exemplary methods of utilizing a user input included as part of a wireless tag.
FIG. 13B illustrates exemplary methods of utilizing a user input included as part of a wireless tag.

FIG. 13 illustrates exemplary methods of utilizing a user input 610 included as part of wireless tag 40. An exemplary wireless tag 40 is illustrated as including user input 610. Exemplary user inputs 610 include buttons, touch screens, remote-touch and touchless surfaces. Other suitable user inputs, such as those described with regard to user interface 54, may also be used.

An exemplary process for taking a predetermined action 620 is illustrated in FIG. 13A. Block 622 illustrates associating wireless tag 40 with a device, such as electronic device 10 or external device 30, as in block 204 of FIG. 5. In block 624, controller 28 monitors the data sent from radio transceiver 56 received by radio transceiver 24 for a predetermined signal. Controller 48 commands radio transceiver 56 to send the predetermined signal upon a signal received from user input 610. In one embodiment, user input 610 sends the signal to controller 48 upon user input 610 being touched a single time. In another embodiment, user input 610 sends the signal to controller 48 upon user input 610 being touched one or more times. Being touched may include a user pressing or clicking user input 610 as a button, or touching or pointing to user input 610 as an icon on a screen. In block 626, if controller 48 does not detect the predetermined signal, the system returns to block 624 to monitor. If the signal is received, in block 628 a predetermined action is taken. Predetermined actions may include, but are not limited to, recording data on electronic device 10, sending data to external device 30, recording data from sensor 42, recording the location of electronic device 10, purchasing an item, sending or receiving a payment, or sounding alarm 16 or alarm 46.

An exemplary process 630 for associating wireless tag 40 with a device, such as electronic device 10 or external device 30 is illustrated in FIG. 13B. If wireless tag 40 is to be secured to an object, block 632 illustrates securing wireless tag 40 to object 70. In another embodiment, wireless tag 40 is not secured to an object 70, and block 632 is omitted. In block 634, wireless tag 40 is associated with electronic device 10. In block 636, controller 28 monitors the data sent from radio transceiver 56 received by radio transceiver 24 for a predetermined signal. In one embodiment, controller 48 commands radio transceiver 56 to send the predetermined signal upon a signal received from user input 610. User input 610 sends the signal to controller 48 upon user input 610 being touched. Being touched may include a user pressing or clicking user input 610 as a button, or touching or pointing to user input 610 as an icon on a screen. In block 638, if controller 48 does not detect the predetermined signal, the system returns to block 624 to monitor. If the signal is received, in block 640 controller 48 associates wireless tag 40 with external device 30. In another embodiment, a controller and radio transceiver associated with external device 30 perform as controller 48 and radio transceiver 48 above and associates wireless tag 40 with external device 30.

Figure 14A:
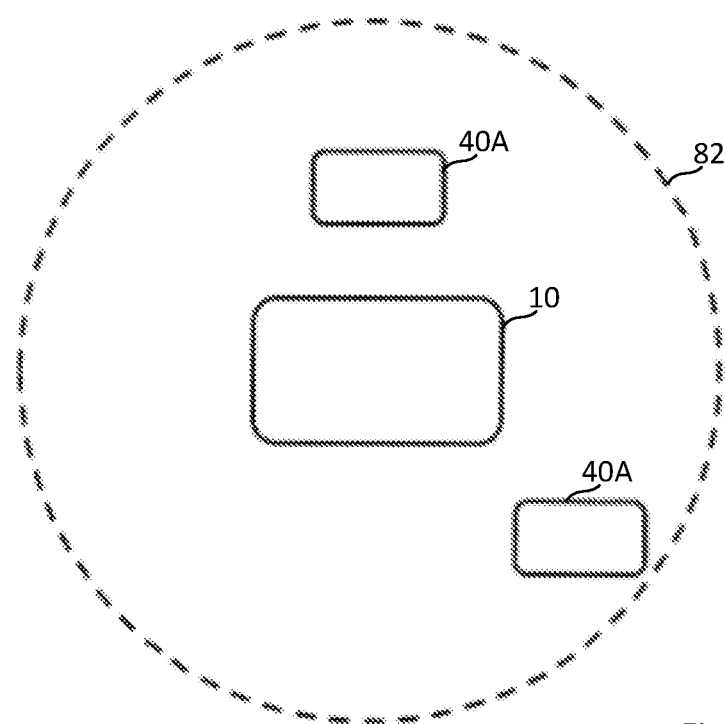
FIG. 14A illustrates an anti-theft or anti-loss embodiment of the disclosed system.
Figure 14B:
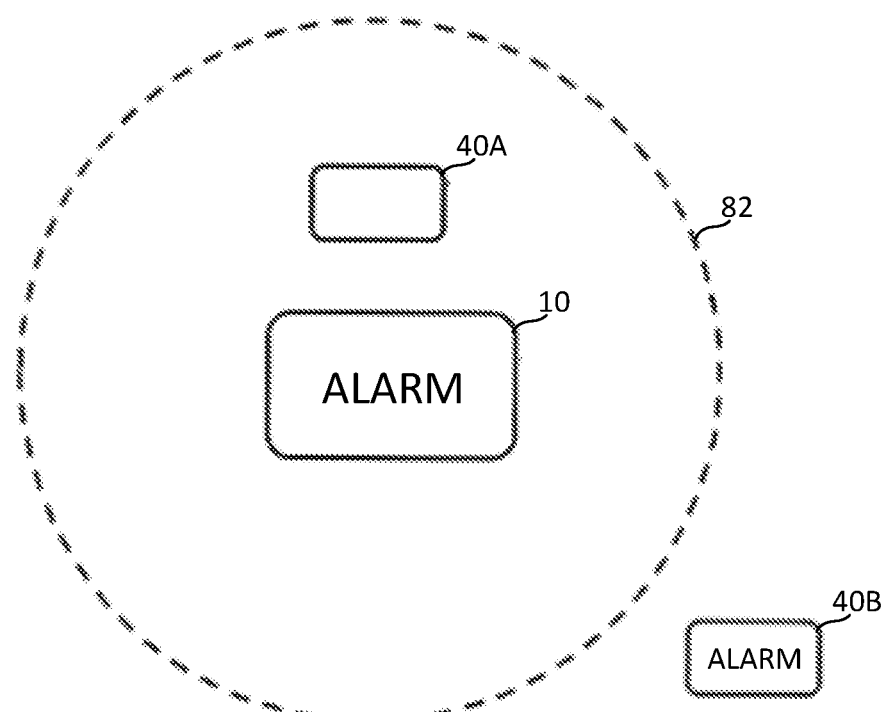
FIG. 14B illustrates an anti-theft or anti-loss embodiment of the disclosed system.

FIG. 14 illustrates an anti-theft or anti-loss embodiment of the disclosed system. In FIG. 14 A, wireless tags 40A, 40B are less than a predetermined distance or range 82 from electronic device 10. In FIG. 14B, wireless tag 40B is more than a predetermined distance or range 82 from electronic device 10. Alarm 16 on electronic device 10 and alarm 46 on tag 40B are activated, while alarm 46 on tag 40A is not activated.

In another embodiment, an electronic device 10 may activate alarm 46 when a wireless tag 40 returns to within a predetermined distance or range of electronic device 10. This embodiment may be used with previously associated or unassociated tags. In one embodiment, a previously associated tag 40 is attached to a piece of luggage, which is then taken out of the predetermined distance or range from electronic device 10. When tag 40 and attached luggage re-enter the predetermined distance or range from electronic device 10, such as in a baggage claim area for example, either alarm 16 on electronic device 10 or alarm 46 on tag 40 or both are activated.

Figure 15:
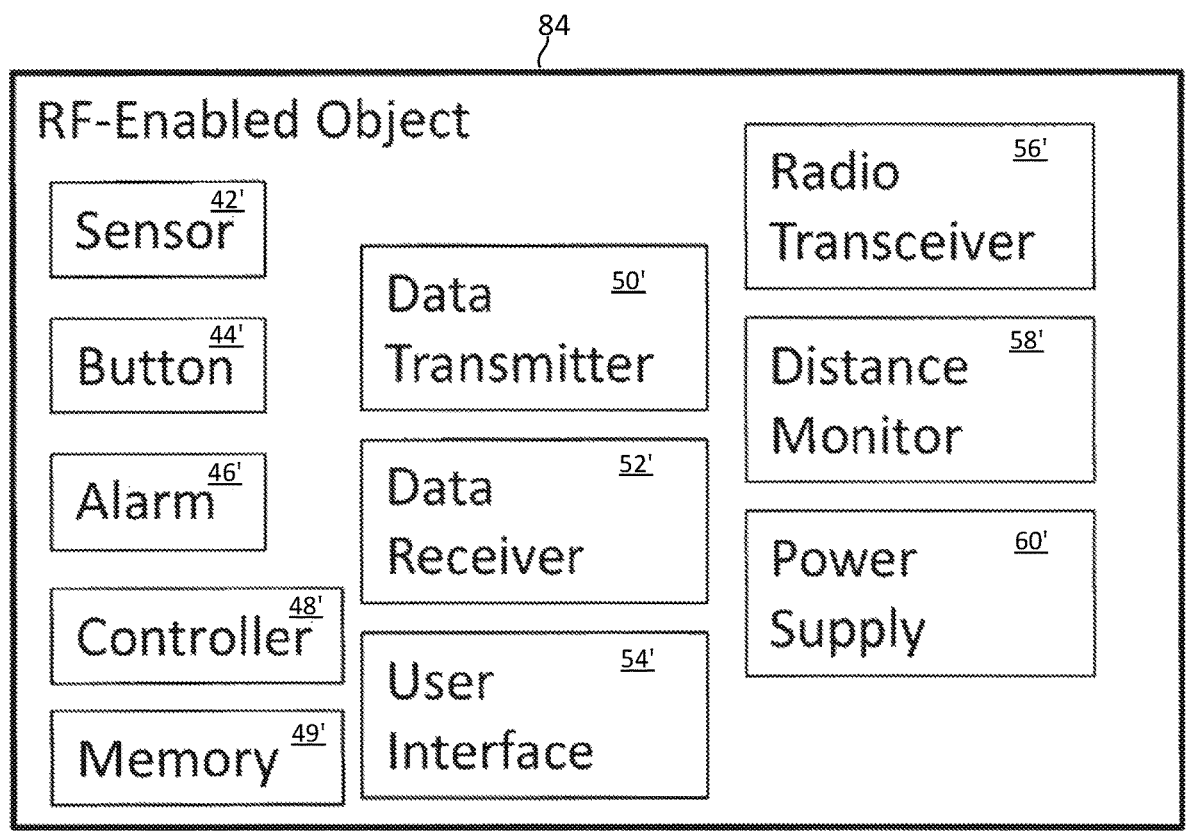
FIG. 15 illustrates an exemplary RF-enabled object for wireless communication with an electronic device or network.

Referring next to FIG. 15, an exemplary embodiment of an RF-enabled object 84 according to the present disclosure is disclosed. The RF-enabled object 84 is similar to the combination of the wireless tag 40 coupled to the object 70 described in FIG. 2A above. Similar to wireless tag 40, RF-enabled object 84 in some embodiments includes controller 48' controlling radio transceiver 56' and power supply 60'. RF-enabled object 84 may additional include memory 49'. Memory 49' includes instructions executed by controller 48'. Radio transceiver 56' sends and/or receives data from other radio transceivers, including radio transceiver 24 incorporated in electronic device 10. In one embodiment, radio transceiver 56' is a Bluetooth (R) transceiver that operates on Bluetooth protocols. In another embodiment, radio transceiver 56' operates on RF protocols. In still another embodiment, radio transceiver 56' operates on NFC protocols. Other suitable radio transceivers may also be used. In one embodiment, at least some of the data exchanged is encrypted. Exemplary RF-enabled objects 84 include Bluetooth, NFC or RF enabled devices such as phones, tablets, goggles, watches, electronics, and other suitable objects.

Similar to wireless tag 40, RF-enabled object 84 may include one or more of sensors 42', a user interface 54' comprising one or more I/O modules including alarm 46' and button 44', distance monitor 58', data transmitter 50', and data receiver 52'. In yet still another embodiment, RF-enabled object 84 may include a GPS or other suitable location detection technologies (not shown).

RF-enabled object 84 collects status and position data similar to the previously described ways wireless tag 40 collects status and position data. Exemplary data include data similar to that illustrated in FIGS. 3 and 4 corresponding to the RF-enabled object 84 rather than wireless tag 40. Other exemplary data include the time, the absolute position and direction determined by electronic device 10, the status of one or more RF-enabled objects 84 as in range/out of range as determined by the electronic device 10, data from one or more sensors 42' attached to or integrated in RF-enabled object 84, and the status of any command executed by controllers 28 and/or 48'.

FIGS. 16A and 16B illustrate exemplary processes 700, 720 of the RF-enabled object 84 system in an anti-theft or anti-loss embodiment. Process 700 for RF-enabled object 84 is similar to process 200 for wireless tag 40 discussed above in relation to FIG. 5A. Process 720 for RF-enabled object 84 is similar to process 220 for wireless tag 40 discussed above in relation to FIG. 5B.

In FIG. 16A, the block 704 illustrates associating RF-enabled object 84 with electronic device 10. In one embodiment, block 704 includes selecting a name and/or icon for RF-enabled object 84. In another embodiment, associating RF-enabled object 84 is performed through a user interface 22 on electronic device 10. In block 706, a range or distance between RF-enabled object 84 and electronic device 10 is selected. In block 708, the connection between RF-enabled object 84 and electronic device 10 is monitored by both controller 28 of electronic device 10 and controller 48' of RF-enabled object 84. If the connection between radio transceiver 24 and radio transceiver 56' is broken as shown in block 710, an alarm is activated in block 716 and data is saved in block 718. If in block 710 the connection is not broken, in block 712 the distance between electronic device 10 and RF-enabled object 84 as determined by distance monitor 26 is monitored. As shown in block 714, if the distance is less than the distance or range selected in block 706, the system returns to block 708 to monitor the connection. If the distance is not less than the set distance or range, an alarm is activated in block 716 and data is saved locally to electronic device 10 and sent to external device 30 as described above. In another embodiment (not shown) an additional predetermined action is taken or command is activated in addition to the alarm and data communication.

FIG. 16B illustrates a variant process 720 of the exemplary anti-loss or anti-theft process described above. In the process illustrated in FIG. 16B, if the distance or range in block 714 is less than the distance selected in block 706, in block 719 data is saved locally to electronic device 10 and sent to external device 30 as in block 718 before returning to block 708 to monitor the connection.

FIGS. 16C and 16D illustrate additional variant process 722, 724 of the exemplary anti-loss or anti-theft processes 700, 720 of FIGS. 16A and 16B. Process 722 is similar to process 700, and process 724 is similar to process 720. In both processes 722 and 724, in block 707, in addition to the range or distance between RF-enabled object 84 and electronic device 10 is selected as in block 706 of FIG. 16A, a profile is selected. In one embodiment, a profile is a set settings, where each setting is an action based on a predetermined condition. Exemplary settings include whether to alarm or not based on a predetermined condition, such as the location, the time, the temperature, etc. One exemplary setting is to disable the alarm during the weekends. Another exemplary setting is to disable the alarm in a predetermined location, such as a user's work. In these embodiments, if the connection is broken in block 710, or if the distance is less than the set range/distance in block 714, block 724 first determines whether the current profile settings allow for an alarm. If the profile allows for an alarm, the alarm is activated in block 716 as in FIG. 16A. If the profile does not allow for an alarm, the system returns to block 708 to monitor the signal.

Figure 17:
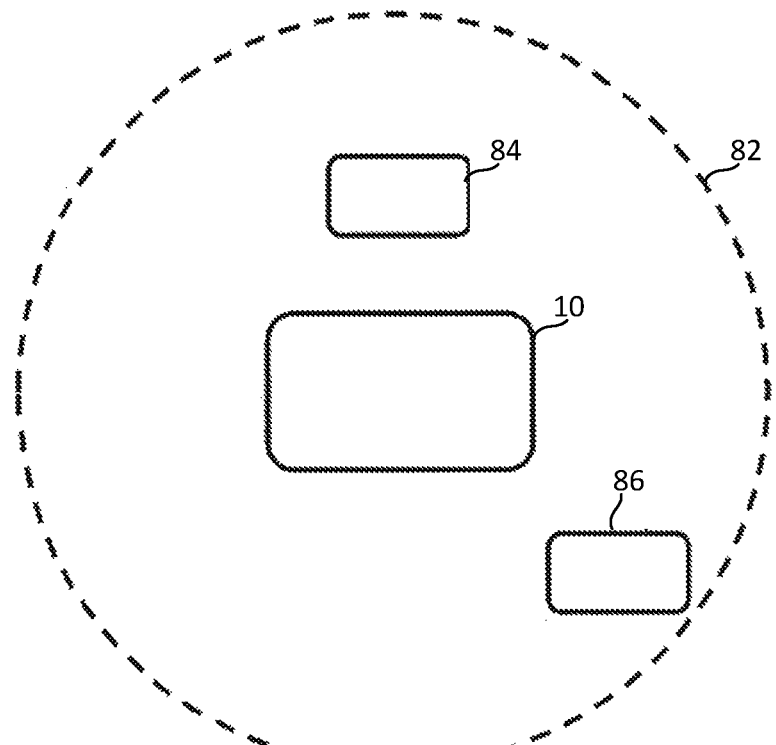
FIG. 17 illustrates an anti-theft or anti-loss embodiment of the disclosed RF-enabled object system.
Figure 17:
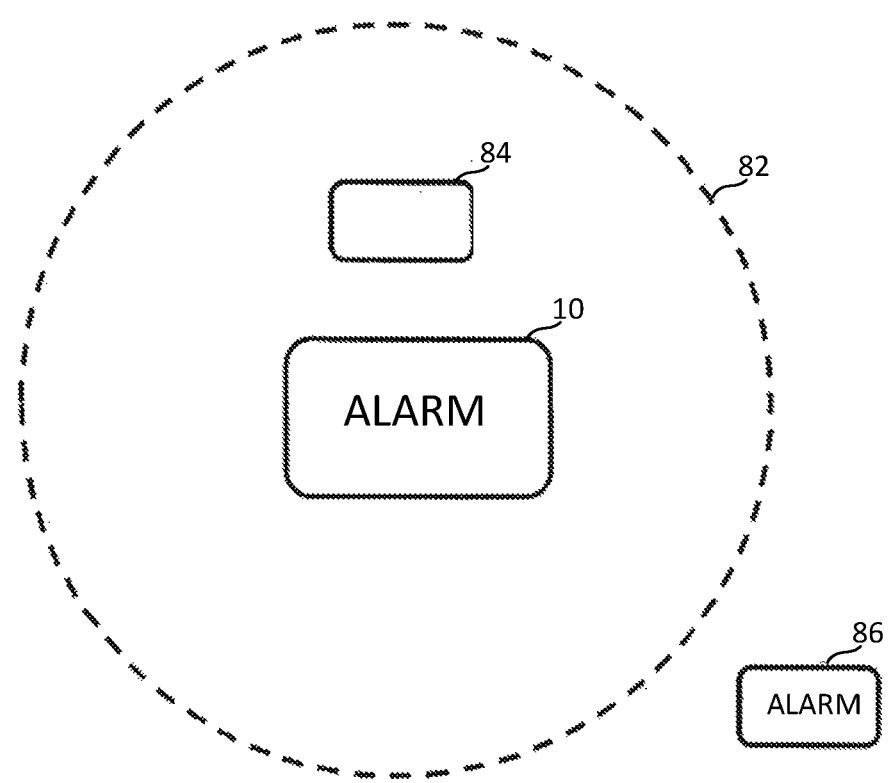

FIGS. 17A and 17B illustrate an anti-theft or anti-loss embodiment of the disclosed system for RF-enabled objects 84 similar to FIGS. 14A and 14B for wireless tags 40. In FIG. 17A, RF-enabled objects 84, 86 are less than a predetermined distance or range 82 from electronic device 10. In FIG. 17B, RF-enabled object 86 is more than a predetermined distance or range 82 from electronic device 10. Alarm 16 on electronic device 10 and alarm 46' on RF-enabled object 86 are activated, while alarm 46' on RF-enabled object 84 is not activated. In one embodiment, at least one of electronic device 10 and RF-enabled object 86 update and save the time alarm 46' was activated and the location of electronic device 10 when alarm 46' was activated to an external device 30.

The exemplary processes illustrated in FIGS. 5-11 may similarly be implemented using RF-enabled object 84 in place of wireless tag 40 secured to an object 70.

Figure 18:
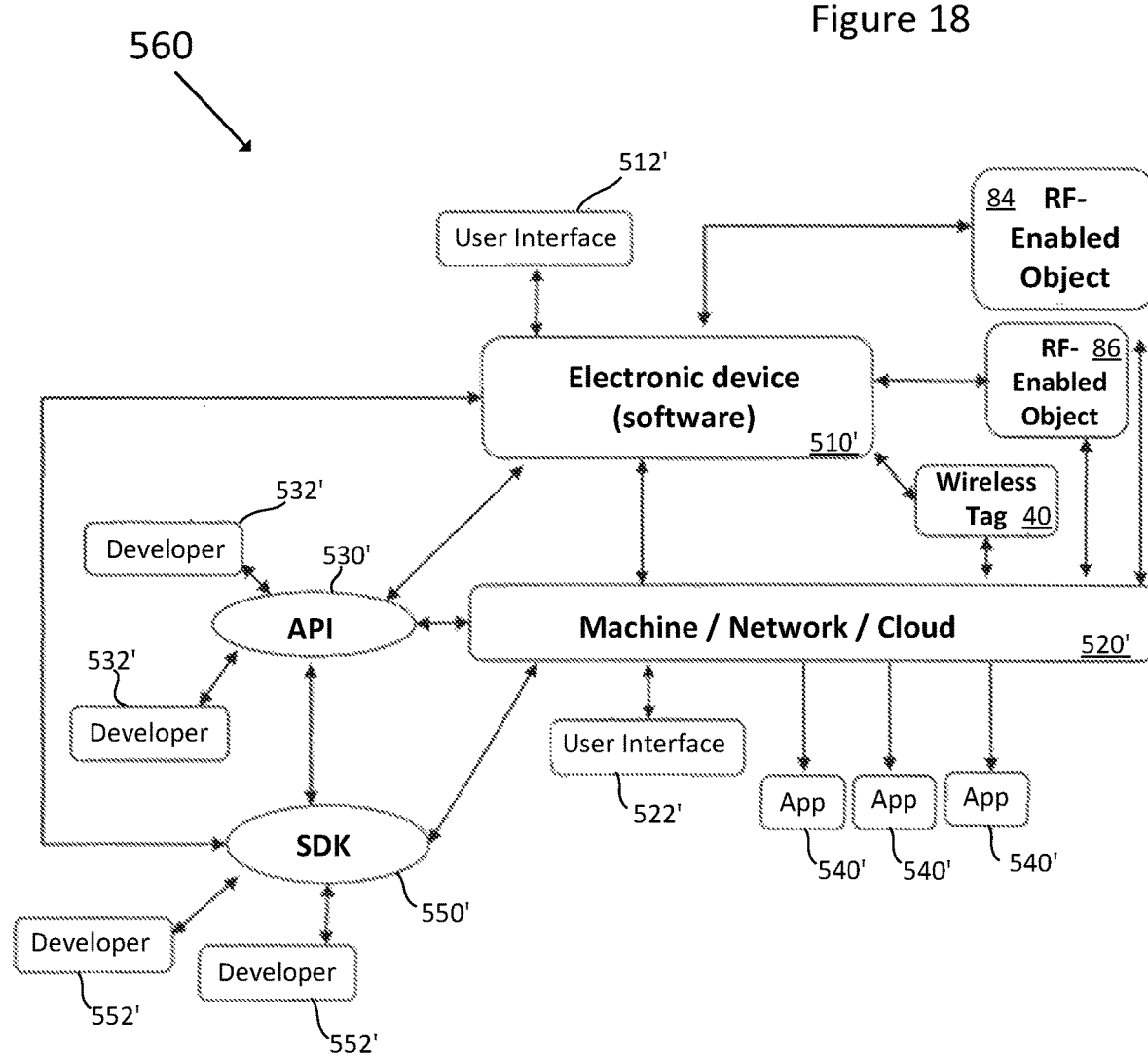
FIG. 18 illustrates an exemplary system architecture for providing an application programming interface and software development kit to developers for the disclosed system including both wireless tags and RF-enabled objects.

FIG. 18 illustrates a system architecture 560 similar system architecture 500 to that illustrated in FIG. 12. Within the exemplary system architecture 560, both wireless tags 40 and RF-enabled objects 84 and 86 are provided. Additional wireless tags 40 and RF-enabled objects 84 may also be provided. RF-enabled objects 84, 86, and wireless tag 40 are in communication with electronic device 510'. In one embodiment, electronic device 510' is an electronic device 10 as previously described. Electronic device 510' includes a software program or application for communicating with RF-enabled objects 84, 86, wireless tag 40, and a machine/network/cloud 520'. In one embodiment, machine/network/cloud 520' is an external device 30.

The software program or application includes a user interface 512'. In one embodiment, user interface 512' is user interface 22. Machine/network/cloud 520' also includes a user interface 522'. In one embodiment, user interfaces 512', 522' provide access to data, programs, and applications stored locally on electronic device 510' and machine/network/cloud 520'.

In one embodiment, user interface 522' allows a user to view, query, organize, and categorize data stored on external device 520' gathered through data sent by electronic devices 510', RF-enabled objects 84, 86, and wireless tag 40. In another embodiment, user interface 522' can be used to initiate commands or activate alarms on RF-enabled objects 84, 86, wireless tag 40, and electronic device 510'. In still another embodiment, user interface 522' allows a user to lock, program the device, initiate an action, remotely backup or wipe reset electronic device 510' having a software program or application for communicating with wireless tags 40.

In one exemplary embodiment, system architecture 560 includes an API 530'. API 530' is similar to API 530 described in relation to FIG. 12. In another exemplary embodiment, system architecture 560 includes a software development kit (SDK) 550'. SDK 550' is similar to SDK 550 described in relation FIG. 12.

Applications 540' may be downloaded by users to their electronic device such as that shown in 510', to a machine/network/cloud such as that shown in 520', or reside on a machine/network/cloud for access through a web browser or other suitable software and/or user interface from an electronic device, such as 510', or a server.

In one exemplary embodiment, system architecture 560 allows for access to RF-enabled objects 84, 86 for use in application 540'. The machine/network/cloud 520' can be configured to grant access or set permissions to allow certain users access to modules or allow different users different types or levels of access of RF-enabled objects 84, 86, including sensors 42', alarms 46', controllers 48', data transmitters 50', data receivers 52', user interface 54', radio transceiver 56', distance monitor 58', and power supply 60', and other suitable modules. Additional suitable modules include, but are not limited to, cameras and microphones. Applications 540' can be thus designed to use the modules of RF-enabled objects 84, 86.

In another exemplary embodiment, system architecture 560 allows for a user to set one or more sets of permissions based on the current status of one or more modules of wireless tags 40, 502, 504, and RF-enabled objects 84, 86, including sensors 42 42', alarms 46 46', controllers 48 48', data transmitters 50 50', data receivers 52 52', user interface 54 54', radio transceiver 56 56', distance monitor 58 58', and power supply 60 60'.

In an exemplary embodiment, a first set of users is provided permissions to access the certain recorded data from wireless tag 40 or RF-enabled object 84 when under a first condition, and a second set of users is provided permissions to access the certain recorded data from wireless tag 40 or RF-enabled object 84 when under a second condition.

In a more particular embodiment, only the owner of electronic device 10 is granted access to view a history of locations and times recorded from electronic device 10, wireless tags 40, or RF-enabled objects 84 as long as wireless tags 40 or RF-enabled objects 84 do not exceed a predetermined distance from electronic device 10. If the predetermined distance from electronic device 10 has been exceeded, a larger group of users, for examples friends, authorities, co-workers, or other designated individuals or groups to whom the owner has selected, can then access the history of locations and times recorded from electronic device 10, wireless tags 40, or RF-enabled objects 84 from the alarm position forward in time. In this way, the friends can assist the owner in locating or recovering the wireless tag 40 or RF-enabled object 84 which was taken beyond the predetermined distance.

In another more particular embodiment, once a wireless tag 40 or active device 84 has exceeded a predetermined distance from electronic device 10, wireless tag 40 or active device 84 is configured to be detectable by multiple radio transceiver systems. Thus, an unassociated radio transceiver 24 or data receiver 20 associated with a second electronic device 10 in communication with external device 30 is able to detect a predetermined radio signal or type of signal from wireless tag 40 or active device 84 and upload and save the current location of the wireless tag 40 or active device 84 to the external device 30. In this way, the location of wireless tag 40 or active device 84 can be updated on the external device 30 or machine/network/cloud 520 520', allowing the owner of wireless tag 40 or active device 84 to monitor its location even when wireless tag 40 or active device 84 is not in contact with electronic device 10.

While this invention has been described as relative to exemplary designs, the present invention may be further modified within the spirit and scope of this disclosure. Further, this application is intended to cover such departures from the present disclosure as come within known or customary practice in the art to which this invention pertains.

What is claimed is:

1. A system for detecting placement or misplacement of an object, the system comprising:
a wireless tag associated with the object;
a first set of instructions stored in a first non-transitory storage medium, the first set of instructions, when executed by one or more processors in a first electronic device associated with the wireless tag, cause the one or more processors in the first electronic device to automatically:
determine a position of the first electronic device;
determine a status of the wireless tag, the status being "in range" when the first electronic device and the wireless tag are within a predetermined range and "out of range" when the first electronic device and the wireless tag are outside of the predetermined range; and
transmit the position of the first electronic device and the status to an external electronic device in response to the status being "in range"; and
transmit the position of the first electronic device and the status to the external electronic device in response to the status being "out of range";
additional instructions stored in non-transitory storage media of a plurality of additional electronic devices which are unassociated with the wireless tag, the additional instructions, when executed by one or more processors in the plurality of additional electronic devices, enable each additional electronic device to automatically:
determine a position of the additional electronic device;
determine an identifier for the wireless tag using one or more signals from the wireless tag; and
transmit the position of the additional electronic device and the identifier to the external electronic device;
wherein the wireless tag includes a controller configured to:
determine, in response to a strength or absence of signals communicated with the first electronic device and the wireless tag, that the status of the wireless tag is "out of range"; and
render the wireless tag automatically detectable by all of the plurality of additional electronic devices in response to determining that the status of the wireless tag out of range;"
wherein the additional instructions, when executed by the one or more processors in the plurality of additional electronic devices, cause each additional electronic device to respond to automatic detection of the wireless tag by uploading a location of the wireless tag to the external electronic device thereby allowing the uploaded location of the wireless tag to be determined for an owner of the wireless tag or any other entity with sufficient permission when the status of the wireless tag is "out of range;" and
wherein the external electronic device is configured to communicate the uploaded location of the wireless tag to the first electronic device.

2. A system for detecting placement or misplacement of an object, the system comprising:
a wireless tag associated with the object;
a first set of instructions stored in a first non-transitory storage medium, the first set of instructions, when executed by one or more processors in a first electronic device associated with the wireless tag, cause the one or more processors in the first electronic device to automatically:

determine a position of the first electronic device;
determine a status of the wireless tag, the status being "in range" when the first electronic device and the wireless tag are within a predetermined range and "out of range" when the first electronic device and the wireless tag are outside of the predetermined range; and
transmit the position of the first electronic device and the status to an external electronic device in response to the status being "in range"; and
transmit the position of the first electronic device and the status to the external electronic device in response to the status being "out of range";
additional instructions stored in non-transitory storage media of a plurality of additional electronic devices which are unassociated with the wireless tag, the additional instructions, when executed by one or more processors in the plurality of additional electronic devices, enable each additional electronic device to automatically:
determine a position of the additional electronic device;
determine an identifier for the wireless tag using one or more signals from the wireless tag; and
transmit the position of the additional electronic device and the identifier to the external electronic device;
wherein the wireless tag includes a controller configured to:
determine, in response to a strength or absence of signals communicated with the first electronic device and the wireless tag, that the status of the wireless tag is "out of range"; and
render the wireless tag automatically detectable by all of the plurality of additional electronic devices in response to determining that the status of the wireless tag is "out of range;"
wherein the additional instructions, when executed by the one or more processors in the plurality of additional electronic devices, cause each additional electronic device to respond to automatic detection of the wireless tag by uploading a location of the wireless tag to the external electronic device thereby allowing the uploaded location of the wireless tag to be determined for an owner of the wireless tag or any other entity with sufficient permission when the status of the wireless tag is "out of range;" and
wherein the first set of instructions, when executed by the one or more processors in the first electronic device associated with the wireless tag, cause the one or more processors in the first electronic device to communicate a way to the wireless tag using the uploaded location of the wireless tag.

3. A software module for detecting placement or misplacement of a plurality of objects associated with a plurality of wireless tags, the software module comprising a first set of instructions stored in a tangible, non-transitory storage medium that, when executed by one or more processors of a first electronic device, causes the one or more processors to automatically:
communicate signals with a radio transceiver of one or more wireless tags of the plurality of wireless tags;
determine a status for the one or more wireless tags of the plurality of wireless tags, the status being "in range" when the first electronic device and the wireless tag are within a predetermined range and "out of range" when the first electronic device and the wireless tag are outside the predetermined range;
wherein each of the one or more wireless tags includes a controller configured to:
determine, in response to a strength or absence of signals communicated with the first electronic device and the wireless tag, that the status of the wireless tag is "out of range"; and
render the wireless tag automatically detectable by two or more additional electronic devices unassociated with the wireless tag in response to determining that the status of the wireless tag is "out of range";
the software module comprising a second set of instructions stored in a tangible, non-transitory storage medium that, when executed by one or more processors of each of the two or more additional electronic devices, enables the one or more processors to automatically;
communicate data for a wireless tag rendered automatically detectable by the controller of the wireless tag to an external device in response to detecting that the wireless tag and the additional electronic device are within a predetermined range, the data including:
the position of the additional electronic device; and
a status of the wireless tag;
wherein the data communicated to the external device further includes:
an identifier for the wireless tag; and
a time indicator for the wireless tag, the time indicator identifying when the additional electronic device detected that the wireless tag and the additional electronic device are within the predetermined range.

4. A software module for detecting placement or misplacement of a plurality of objects associated with a plurality of wireless tags, the software module comprising a first set of instructions stored in a tangible, non-transitory storage medium that, when executed by one or more processors of a first electronic device, causes the one or more processors to automatically:
communicate signals with a radio transceiver of one or more wireless tags of the plurality of wireless tags;
determine a status for the one or more wireless tags of the plurality of wireless tags, the status being "in range" when the first electronic device and the wireless tag are within a predetermined range and "out of range" when the first electronic device and the wireless tag are outside the predetermined range;
wherein each of the one or more wireless tags includes a controller configured to:
determine, in response to a strength or absence of signals communicated with the first electronic device and the wireless tag, that the status of the wireless tag is "out of range"; and
render the wireless tag automatically detectable by two or more additional electronic devices unassociated with the wireless tag in response to determining that the status of the wireless tag is "out of range";
the software module comprising a second set of instructions stored in a tangible, non-transitory storage medium that, when executed by one or more processors of each of the two or more additional electronic devices, enables the one or more processors to automatically;
communicate data for a wireless tag rendered automatically detectable by the controller of the wireless tag to an external device in response to detecting that the wireless tag and the additional electronic device are within a predetermined range, the data including:
the position of the additional electronic device; and a status of the wireless tag;

wherein the second set of instructions, when executed by the one or more processors of each of the two or more additional electronic devices, causes the one or more processors, in response to determining that a status for one or more wireless tags has changed, to activate an interface between an operator and the wireless tag, the operator being at least one of a human operator, a computer, a machine, or a software application interfacing with the wireless tag, the two or more additional electronic devices or the external device.

5. A system for detecting placement or misplacement of an object, the system comprising:

a wireless tag associated with the object, the wireless tag including an internal power source and a radio transceiver; and a first set of instructions stored in a tangible, non-transitory storage medium that, when executed by one or more processors in a first electronic device, cause the one or more processors to automatically:

determine a position of the first electronic device;

determine a status of the wireless tag based upon a strength or absence of signals communicated with the radio transceiver of the wireless tag and a radio transmitter of the first electronic device, the status being "in range" when the first electronic device and the wireless tag are within a predetermined range and "out of range" when the first electronic device and the wireless tag are outside the predetermined range;

communicate data, including the position of the first electronic device and the status to an external electronic device or network in response to the status being "in range";

communicate data, including the position of the first electronic device and the status to the external electronic device or network in response to the status being "out of range";

a second set of instructions that, when executed by one or more processors in a plurality of additional electronic devices which are unassociated with the wireless tag, enable each of the additional electronic devices to automatically:

determine a position of the additional electronic device;

determine an identifier of the wireless tag using communicated signals from the radio transceiver of the wireless tag; and communicate the determined identifier and the position of the additional electronic device to the external electronic device or network;

wherein the wireless tag includes a controller configured to:

determine, in response to a strength or absence of signals communicated with the first electronic device and the wireless tag, that the status of the wireless tag is "out of range"; and render the wireless tag automatically detectable by all of the plurality of additional electronic devices in response to determining that the status of the wireless tag is "out of range;"

wherein the determined status includes a time record indicating a time when the wireless tag and the first electronic device are within a predetermined range or a time when the wireless tag and the first electronic device are outside of the predetermined range.

* * * * *